(12) United States Patent
Earney et al.

(10) Patent No.: US 10,005,083 B2
(45) Date of Patent: Jun. 26, 2018

(54) OPTICAL ALIGNMENT TOOL

(71) Applicant: Illumina, Inc., San Diego, CA (US)

(72) Inventors: John Earney, San Diego, CA (US);
Dakota Watson, San Diego, CA (US);
Joseph Pinto, Solana Beach, CA (US)

(73) Assignee: ILLUMINA, INC., San Diego, CA (US)

( * ) Notice: Subject to any disclaimer, the term of this patent is extended or adjusted under 35 U.S.C. 154(b) by 5 days.

(21) Appl. No.: 15/382,684

(22) Filed: Dec. 18, 2016

(65) Prior Publication Data

US 2017/0151565 A1    Jun. 1, 2017

Related U.S. Application Data

(63) Continuation of application No. 14/906,536, filed as application No. PCT/US2014/053124 on Aug. 28, 2014, now Pat. No. 9,540,690.

(Continued)

(51) Int. Cl.
| | |
|---|---|
| H04N 9/47 | (2006.01) |
| H04N 7/18 | (2006.01) |
| B01L 3/00 | (2006.01) |
| G01N 21/64 | (2006.01) |
| C12Q 1/68 | (2018.01) |
| G01N 21/05 | (2006.01) |
| H04N 17/00 | (2006.01) |

(52) U.S. Cl.
CPC ... *B01L 3/502715* (2013.01); *B01L 3/502723* (2013.01); *C12Q 1/6874* (2013.01); *G01N 21/05* (2013.01); *G01N 21/645* (2013.01); *G01N 21/6428* (2013.01); *H04N 17/002* (2013.01); *B01L 2300/0816* (2013.01); *B01L 2300/0819* (2013.01); *B01L 2300/0883* (2013.01); *B01L 2300/14* (2013.01); *G01N 2021/058* (2013.01); *G01N 2021/6439* (2013.01); *G01N 2021/6482* (2013.01)

(58) Field of Classification Search
CPC ......... B01L 3/502715; B01L 3/502723; B01L 2300/0883; B01L 2300/0819; B01L 2300/0816; B01L 2300/14; H04N 17/002; C12Q 1/6874; G01N 21/05; G01N 21/645; G01N 21/6428; G01N 2021/058; G01N 2021/6439; G01N 2021/6482
See application file for complete search history.

(56) References Cited

U.S. PATENT DOCUMENTS

2010/0157086 A1    6/2010    Segale et al.

FOREIGN PATENT DOCUMENTS

| WO | 2012096703 A1 | 7/2012 |
|---|---|---|
| WO | 2012170936 A2 | 12/2012 |

OTHER PUBLICATIONS

International Search Report for PCT?US2014/053124 dated Dec. 16, 2014 (3 pages).

(Continued)

*Primary Examiner* — Jared Walker
(74) *Attorney, Agent, or Firm* — Illumina, Inc.

(57) ABSTRACT

Provided is an inspection apparatus including: (a) a translucent or transparent plate having a bottom surface, at least a portion of the bottom surface having an opaque material printed thereon in a pattern having at least one transparent or translucent portion; and (b) a chamber disposed below the bottom surface, whereby light emitted from the chamber or through the chamber can pass through the at least one transparent or translucent portion.

20 Claims, 21 Drawing Sheets

Related U.S. Application Data

(60) Provisional application No. 61/871,181, filed on Aug. 28, 2013.

(56) References Cited

OTHER PUBLICATIONS

Written Opinion of the International Searching Authority for PCT/US2014/053124 dated Dec. 16, 2014 (3 pages).

OPTICAL ALIGNMENT TOOL

This application is based on, and claims the benefit of, U.S. Provisional Application No. 61/871,181, filed Aug. 28, 2013, which is incorporated herein by reference in its entirety.

BACKGROUND

Embodiments of the present disclosure relate generally to apparatus and methods useful for alignment and validation of imaging modules used in, for example, optical detection of samples such as those samples detected in nucleic acid sequencing procedures.

There is a need for tools which facilitate accurate calibration of alignment and validation of optical detection systems. Embodiments of the invention set forth herein satisfy this need and provide other advantages as well.

BRIEF SUMMARY

The present disclosure provides an inspection apparatus including: (a) a translucent or transparent plate having a bottom surface, at least a portion of the bottom surface having an opaque material printed thereon in a pattern having at least one transparent or translucent portion; and (b) a chamber disposed below the bottom surface, whereby light emitted from the chamber or through the chamber can pass through the at least one transparent or translucent portion.

The inspection apparatus can optionally include (c) a fluid filling at least a portion of the channel, the fluid containing at least one light emitting material. The light emitting material can include one or more fluorescent or luminescent molecules. For example, the fluorescent molecules can be a Rhodamine dye or an Oxazine dye.

An inspection apparatus of the present disclosure can also include a second plate in contact with the translucent or transparent plate, wherein the channel opening is disposed between the translucent or transparent plate and the second plate. The channel can be etched in the bottom surface of the translucent or transparent plate or in the top surface of the second plate. In some embodiments the channel is formed by a spacer between the plates.

In particular embodiments, a pattern of opaque material that is on the surface of a plate can include at least one translucent or transparent feature forming a fiducial element in an opaque region.

In particular embodiments, a pattern of opaque material that is on the surface of a plate can include at least one opaque feature forming a fiducial element in a translucent region.

In particular embodiments, a pattern of opaque material that is on the surface of a plate can include a plurality of translucent or transparent holes in an ordered array on an otherwise opaque region.

In particular embodiments, a pattern of opaque material that is on the surface of a plate can include a plurality of opaque patches in an ordered array on an otherwise translucent or transparent region.

An inspection apparatus of the present disclosure can be configured to sit in a flow cell cartridge of a detection instrument.

An inspection apparatus can include a channel that forms a plurality of parallel lanes that are connected to form a single chamber. Optionally, the plurality of parallel lanes can include detection lanes that are relatively wide compared to ingress and egress lanes that are relatively narrow. The ingress and egress lanes can be configured to connect the detection lanes to ingress and egress ports respectively.

In some embodiments, a channel present in an inspection apparatus can have an ingress port having a first pressure release port, and an egress port having a second pressure release port. Optionally, the first pressure release port is positioned along a lane that runs in a different direction from the direction of the ingress lane and the ingress port is located at an intersection of the ingress lane and the lane that runs in a different direction from the direction of the ingress lane. For example, the first pressure release port can be positioned along a lane that runs substantially orthogonal to the direction of the ingress lane.

If desired, a second pressure release port can be positioned along a lane that runs in a different direction from the direction of the egress lane and the egress port can be located at an intersection of the egress lane and the lane that runs in a different direction from the direction of the egress lane. For example, the second pressure release port can be positioned along a lane that runs substantially orthogonal to the direction of the egress lane.

In some embodiments a plug material can be present to prevent flow of liquid through a pressure release port, egress port and/or ingress port.

The bottom surface on the top plate of an inspection apparatus can include at least one patterned tile containing an opaque material. Alternatively or additionally, the bottom surface can further include at least one transparent tile that lacks the opaque material.

Optionally, a patterned tile can be entirely coated by the opaque material. Alternatively, the opaque material can include a plurality of transparent or translucent holes having an area less than 75 square microns.

In some embodiments, the opaque material on a tile can include a plurality of transparent or translucent holes that are separated by at least 10 microns. In one example, the opaque material can include a plurality of transparent or translucent holes having an area less than 75 square microns and the opaque material can also include a transparent or translucent window having an area of at least 30,000 square microns.

Optionally, an inspection apparatus can further include at least one fiducial tile having opaque material interrupted by a transparent fiducial having a plus shape. If desired, the tiles on the surface of an inspection apparatus can be arranged in a unit on the bottom surface and the unit can be repeated six times to form a pattern on the bottom surface.

This disclosure also provides an inspection method for validating an imaging module. The method can include steps of (a) positioning an imaging module in optical alignment with an inspection apparatus set forth herein; and (b) detecting light transmitted through one or more of the transparent or translucent portions.

Also provided is an inspection method for aligning a camera in a detection apparatus.

The method can include steps of (a) positioning a camera in optical alignment with an inspection apparatus set forth herein; and (b) detecting light transmitted through one or more of the transparent or translucent portions.

The details of one or more embodiments are set forth in the accompanying drawings and the description below. Other features, objects, and advantages will be apparent from the description and drawings, and from the claims.

DETAILED DESCRIPTION

Figure 1:
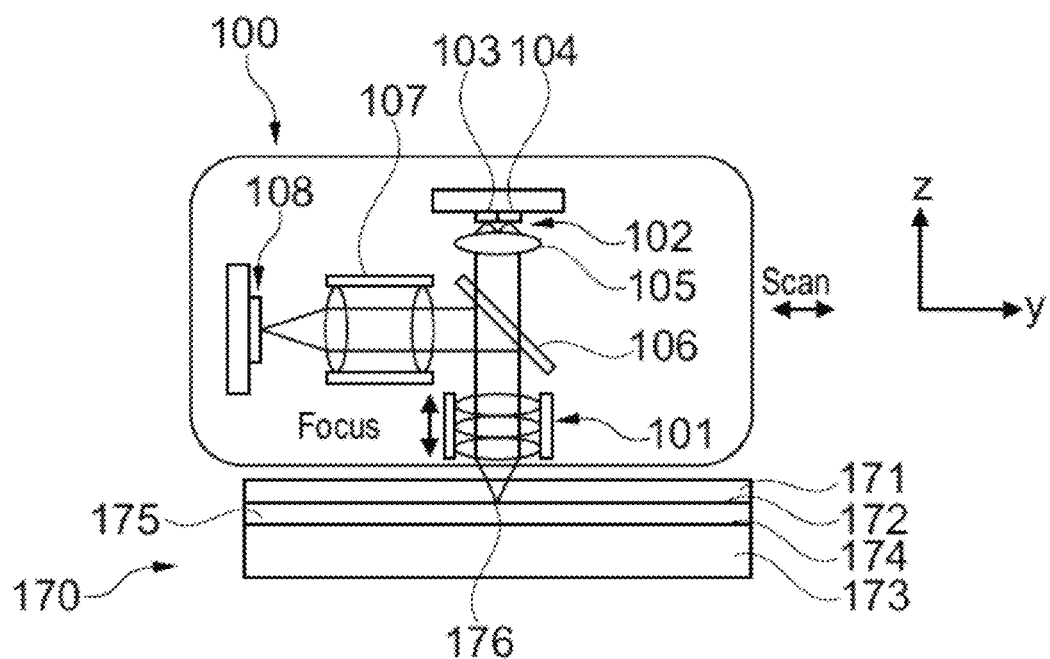
FIG. 1 shows an optical layout for an individual microfluorometer having orthogonal excitation and emission beam paths.

The present disclosure provides an inspection apparatus for alignment (e.g. optical alignment in x, y and/or z dimensions) and validation (e.g. calibration, quantification, or characterization of optical properties) of imaging modules used in, for example, optical detection of samples such as those samples detected in nucleic acid sequencing procedures. The apparatus and methods set forth herein are particularly useful, for example, in alignment and validation for imaging modules set forth in U.S. patent application Ser. No. 13/766,413 filed on Feb. 13, 2013, published as US 2013/0260372 A1, and entitled "INTEGRATED OPTO-ELECTRONIC READ HEAD AND FLUIDIC CARTRIDGE USEFUL FOR NUCLEIC ACID SEQUENCING," the content of which is incorporated by reference in its entirety.

Imaging Modules and Related Devices

Exemplary embodiments and features of the imaging modules disclosed in US Pat. App. Pub. No. 2013/0260372 A1 are set forth below. However, it will be appreciated that the inspection apparatus and inspection methods set forth herein can be used for alignment and validation of any other suitable imaging module.

This disclosure provides methods and apparatus for high-resolution detection of planar areas such as those present on substrate surfaces. A particularly useful application is optically based imaging of a biological sample that is present on a surface. For example, the methods and apparatus set forth herein can be used to obtain images of nucleic acid features that are present in nucleic acid arrays, such as those used in nucleic acid sequencing applications. A variety of nucleic acid sequencing techniques that utilize optically detectable samples and/or reagents can be used. These techniques are particularly well suited to the methods and apparatus of the present disclosure and therefore highlight various advantages for particular embodiments of the invention. Some of those advantages are set forth below for purposes of illustration and, although nucleic acid sequencing applications are exemplified, the advantages can be extended to other applications as well.

In regard to some of the examples set forth herein, salient characteristics of many nucleic acid sequencing techniques are (1) the use of multicolor detection (e.g. often four different fluorophores are used, one for each of the different nucleotide types A, C, G and T (or U) present in nucleic acids), (2) distribution of large numbers of different fragments from a nucleic acid sample (e.g. fragments from a genome sample, RNA sample, or derivative thereof) onto the surface of an array and (3) repeated cycles of fluidic processing and imaging of the arrays. Embodiments of the methods and apparatus disclosed herein are particularly useful for nucleic acid sequencing because they can provide the capability of high resolution imaging of array surfaces in multiple colors and in multiple repetitions. For example, embodiments set forth herein allow an image of a surface to be obtained at a resolution that is in the range of hundreds, tens or even single digit microns. As such, nucleic acid features having nearest neighbor, average center-to-center spacing that is lower than 100 microns, 50 microns, 10 microns, 5 micron or fewer can be resolved. In particular embodiments, wide-field images of surfaces can be acquired, including for example, images that cover an area of 1 mm$^2$ or more of an array. The images can be acquired in multiple colors simultaneously or sequentially, for example, to identify fluorescent labels uniquely associated with different nucleotide types. Moreover, images can be acquired sequentially for multiple cycles of a sequencing technique. The images from a given area of the array can be reliably compared from each cycle to determine the sequence of color changes detected for each nucleic acid feature on the array. The sequence of color changes can in turn be used to infer the sequences of the nucleic acid fragments in each feature.

In particular embodiments, an apparatus of the present disclosure includes one or more microfluorometers. Each of the micro fluorometers can include an excitation radiation source, a detector and an objective to form an integrated subunit of a read head. Other optical components can be present in each microfluorometer. For example a beam splitter can be present to provide for a compact epifluorescent detection configuration, whereby the beam splitter is positioned to direct excitation radiation from the excitation radiation source to the objective and to direct emission radiation from the objective to the detector.

An advantage of using an integrated microfluorometer design is that the microfluorometer can be conveniently moved, for example in a scanning operation, to allow imaging of a substrate that is larger than the field of view of the microfluorometer. In particular embodiments, several microfluorometers can be combined to form a read head. Various configurations for the combination of read heads are set forth below and can be selected to suit a particular format for a substrate that is to be imaged, while maintaining relatively compact size for the overall read head. The relatively small size and low mass of the read head in several embodiments of the present disclosure results in relatively low inertia such that the read head comes to rest quickly after being moved, thereby favoring rapid scanning of a nucleic acid array or other substrate. In some cases, the micro fluorometers can be affixed to a carriage such that they are not independently moveable in at least some dimensions during the course of an analytical application such as a nucleic acid sequencing run. For example, multiple microfluorometers can be permanently fixed such that they are not independently moveable with respect to each other in x and y dimensions (where at least one of x or y is the direction of scan). The microfluorometers may, however, be independently actuated in the z dimension to provide for independent focus control.

Reducing degrees of freedom between several different microfluorometers of an apparatus of the present disclosure provides for protection against loss of alignment during shipping, handling and use of the apparatus.

In some embodiments, multiple microfluorometers that are present in a read head or carriage can each have a dedicated autofocus module. Accordingly, each microfluorometer can be independently focused. In some embodiments, a particular autofocus modules in a read head, although dedicated to actuation of a particular microfluorometer, can nevertheless receive information from at least one other autofocus module in the read head and the information from that particular autofocus module and from the at least one other autofocus module can be used to determine an appropriate actuation to achieve desired focus for the particular microfluorometer. In this way focus for any given microfluorometer can be determined by consensus between two or more microfluorometers present in the same read head or carriage.

Provided herein is a detection apparatus, having (a) a carriage including a plurality of microfluorometers, wherein each of the microfluorometers includes an objective configured for wide-field image detection, wherein the plurality of microfluorometers is positioned to simultaneously acquire a plurality of the wide-field images in a common plane, and wherein each of the wide-field images is from a different area of the common plane; (b) a translation stage configured to move the carriage in at least one direction parallel to the common plane; and (c) a sample stage configured to hold a substrate in the common plane.

A detection apparatus (or an individual microfluorometer) of the present disclosure can be used to obtain one or more images at a resolution that is sufficient to distinguish features on a micron scale. For example, a microfluorometer that is used in a detection apparatus can have a resolution that is sufficient to distinguish features that are separated by at most 500 µm, 100 µm, 50 µm, 10 µm, 5 µm, 4 µm, 3 µm, 2 µm or 1 µm. Lower resolution is also possible, for example, a resolution that distinguishes features that are separated by more than 500µm.

A detection apparatus (or an individual microfluorometer) of the present disclosure is well suited for high-resolution detection of surfaces. Accordingly, arrays having features with average spacing in the micron range are especially useful substrates. In particular embodiments, a detection apparatus or microfluorometer can be used to obtain one or more images of an array having features with center-to-center spacing for nearest neighbors that is on average at or below 500 µm, 100 µm, 50 µm, 10 µm, 5 µm, 4 µm, 3 µm, 2 µm or 1 µm. In many embodiments the features of an array are non-contiguous being separated, for example, by less than 100 µm, 50 µm, 10 µm, 5 µm, 1 µm, or 0.5 µm. However, the features need not be separated. Instead some or all of the features of an array can be contiguous with each other.

Any of a variety of arrays (also referred to as "microarrays") known in the art can be used. A typical array contains features, each having an individual probe or a population of probes. In the latter case, the population of probes at each site is typically homogenous having a single species of probe. For example, in the case of a nucleic acid array, each feature can have multiple nucleic acid species each having a common sequence. However, in some embodiments the populations at each feature of an array can be heterogeneous.

Similarly, protein arrays can have features with a single protein or a population of proteins typically, but not always, having the same amino acid sequence. The probes can be attached to the surface of an array for example, via covalent linkage of the probes to the surface or via non-covalent interaction(s) of the probes with the surface. In some embodiments, probes, such as nucleic acid molecules, can be attached to a surface via a gel layer as described, for example, in US 201 1/0059865 A1, which is incorporated herein by reference.

Whether configured for detection of an array or other sample, one or more microfluorometers that are present in a detection apparatus can be configured for wide-field detection. The field diameter for an individual microfluorometer can be, for example, at least 0.5 mm, 1 mm, 2 mm, 3 mm, 4 mm, 5 mm or larger. By choice of appropriate optical components the field diameter can be limited to a maximum area as well and, as such the field diameter can be, for example, no larger than 5 mm, 4 mm, 3 mm, 2 mm or 1 mm.

Accordingly, in some embodiments an image obtained by an individual microfluorometer can have an area that is in a range of 0.25 $mm^2$ to 25 $mm^2$.

In addition to being configured for wide-field detection, a microfluorometer can be configured to have a numerical aperture (NA) that is greater than 0.2. For example, the NA of an objective used in a microfluorometer of the present disclosure can be at least 0.2, 0.3, 0.4, or 0.5. Alternatively or additionally, it may be desirable to restrict the NA of the objective to be no greater than 0.8, 0.7, 0.6 or 0.5. The methods and apparatus set forth herein are particularly useful when detection occurs through an objective having a NA between 0.2 and 0.5.

In array detection embodiments, a detection apparatus (or individual microfluorometer) can be configured to obtain a digital image of the array. Typically, each pixel of the digital detection apparatus (or individual microfluorometer) will collect signal from no more than a single feature in any given image acquisition. This configuration minimizes unwanted 'cross talk' between features in the image. The number of pixels that detect signal from each feature can be adjusted based on the size and shape of the features imaged and based on the configuration of the digital detection apparatus (or individual microfluorometer). For example, each feature can be detected in a given image by no more than about 16 pixels, 9 pixels, 4 pixels, or 1 pixel. In particular embodiments, each image can utilize on average 6.5 pixels per feature, 4.7 pixels per feature or 1 pixel per feature. The number of pixels used per feature can be reduced, for example, by reducing variability in the position of features in the pattern of the array and tightening the tolerance for alignment of the detection apparatus to the array. Taking as an example a digital detector that is configured to use fewer than 4 pixels per feature, image quality can be improved by using an array of ordered nucleic acid features in place of an array of randomly distributed nucleic acid clusters.

It will be understood that a detection apparatus having multiple microfluorometers can detect an area of a common plane that is roughly equivalent to the number of microfluorometers multiplied by the wide-field area detected by each microfluorometer. The areas need not be contiguous. For example, 2 or more microfluorometers can be positioned to detect discrete regions of a common plane that are separated by an undetected area.

However, if desired, multiple microfluorometers can be positioned to detect areas that are contiguous, but not overlapping. In alternative embodiments a detection apparatus having multiple microfluorometers can detect an area of a common plane that is substantially less than the number of micro fluorometers multiplied by the wide-field area detected by each microfluorometer. This can result, for example, when multiple microfluorometers are positioned to detect areas that have at least a partial overlap. As set forth in further detail elsewhere herein, multiple images need not be acquired in a format that is used for or that even supports reconstruction of a complete image of an array or other common plane that has been detected.

An exemplary optical layout for a microfluorometer 100 is shown in FIG. 1. The microfluorometer 100 is directed to a flow cell 170 having an upper layer 171 and a lower layer 173 that are separated by a fluid filled channel 175. In the configuration shown, the upper layer 171 is optically transparent and the microfluorometer 100 is focused to an area 176 on the inner surface 172 of the upper layer 171. In an alternative configuration the microfluorometer 100 can be focused on the inner surface 174 of the lower layer 173. One or both of the surfaces can include array features that are to be detected by the microfluorometer 100. An inspection apparatus can be used in place of flow cell 170.

The microfluorometer 100 includes an objective 101 that is configured to direct excitation radiation from a radiation source 102 to the flow cell 170 and to direct emission from the flow cell 170 to a detector 108. In the exemplary layout, excitation radiation from the radiation source 102 passes through a lens 105 then though a beam splitter 106 and then through the objective on its way to the flow cell 170. In the embodiment shown the radiation source includes two light emitting diodes (LEDs) 103 and 104, which produce radiation at different wavelengths from each other. For example, a green LED (LEDG) and a red LED (LEDR) can be used. The emission radiation from the flow cell 170 is captured by the objective 101 and is reflected by the beam splitter through conditioning optics 107 and to the detector 108 (e.g. a CMOS sensor). The beam splitter 106 functions to direct the emission radiation in a direction that is orthogonal to the path of the excitation radiation. The position of the objective can be moved in the z dimension to alter focus of the microfluorometer. The microfluorometer 100 can be moved back and forth in the y direction to capture images of several areas of the inner surface 172 of the upper layer 171 of the flow cell 170. Again, an inspection apparatus can be used in place of flow cell 170.

As demonstrated by the exemplary embodiment of FIG. 1, each of the microfluorometers can include a beam splitter and a detector, wherein the beam splitter is positioned to direct excitation radiation from an excitation radiation source to the objective and to direct emission radiation from the objective to the detector. As shown in the figures, each microfluorometer can optionally include an excitation radiation source such as an LED. In this case, each microfluorometer can include a dedicated radiation source, such that the read head includes several radiation sources each separated into individual microfluorometers. In some embodiments, two or more microfluorometers can receive excitation radiation from a common radiation source. As such the two or more microfluorometers can share a radiation source. In an exemplary configuration, a single radiation source can direct radiation to a beam splitter that is positioned to separate the excitation radiation into two or more beams and directs the beams to two or more respective microfluorometers. Additionally or alternatively, excitation radiation can be directed from a radiation source to one, two or more microfluorometers via one or more optical fibers.

It will be understood that the particular components shown in the figures are exemplary and can be replaced with components of similar function. For example, any of a variety of radiation sources can be used instead of an LED. Particularly useful radiation sources are arc lamps, lasers, semiconductor light sources (SLSs), or laser diodes. LEDs can be purchased, for example, from Luminus (Billerica, Mass). Similarly, a variety of detectors are useful including, but not limited to a charge-coupled device (CCD) sensor; photomultiplier tubes (PMT's); or complementary metal-oxide-semiconductor (CMOS) sensor. A particularly useful detector is a 5-megapixel CMOS sensor (MT9P031) available from Aptina Imaging (San Jose, Calif.).

Figure 2:
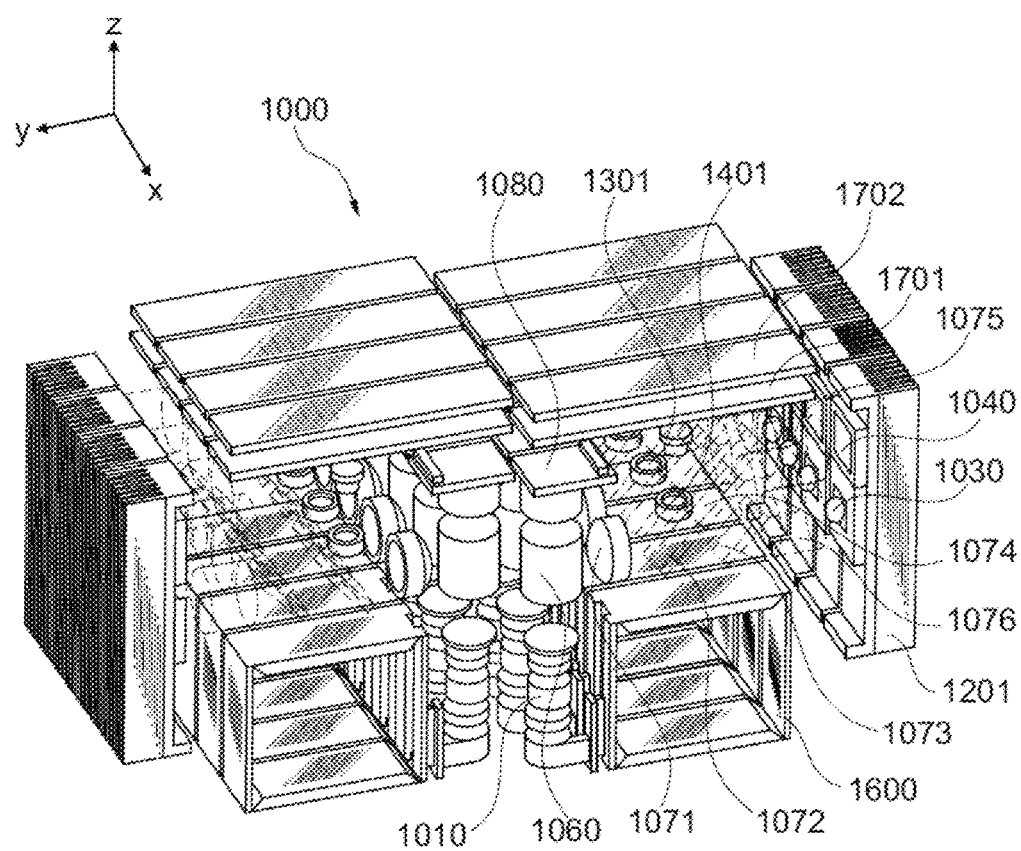
FIG. 2 shows a perspective view of an arrangement of eight micro fluorometers for a detection apparatus.

A perspective view of a read head 1000 having an arrangement of eight microfluorometers is shown in FIG. 2. Each microfluorometer has a compact design. For ease of demonstration the components of only one of the microfluorometers are labeled in FIG. 2 and will be described here. However, as visible in FIG. 2, each of the microfluorometers has similar components and configuration. Two excitation sources are present in each microfluorometer, including a green LED 1040 and a red LED 1030. Excitation light from the LEDs passes through a green LED collector lens 1075 and red LED collector lens 1076, respectively. An LED fold mirror 1074 reflects the green excitation radiation to a combiner dichroic 1073 which reflects the green excitation radiation through a laser diode beam splitter 1072, then through an excitation projection lens 1071 to an excitation/emission dichroic 1060 which reflects the green excitation radiation through an objective 1010. The red excitation radiation passes from the red LED collector lens 1076 to the combiner dichroic 1073 after which the red excitation radiation follows the same path as the green excitation radiation. The objective 1010 is positioned to collect emission radiation and direct it through excitation/emission dichroic 1060 which passes the emission radiation to the CMOS image sensor 1080. A laser diode 1301 is positioned to direct radiation via a laser diode coupling lens group 1401 to laser diode beam splitter 1072 which reflects the laser diode radiation through the excitation projection lens 1071, the excitation/emission dichroic 1060, and the objective 1010. An auto focus module 1600 is coupled to at least part of the objective 1010 and configured to translate the objective 1010 up and down (i.e. along the z dimension). The autofocus module can but need not include components of the auto focus apparatus exemplified previously herein. It will be understood that additional optical components can be present in read head 1000 including, but not limited to those exemplified for FIG. 1.

Furthermore, certain optical components can be absent from read head 1000 or modified in read head 1000 to suit particular applications. Printed circuit boards 1701 and 1702 can be configured to communicate with the detectors, autofocus modules and/or excitation sources.

As demonstrated by the exemplary embodiments above, a read head can include a plurality of objectives, each objective being dedicated to a single microfluorometer. Thus, a microfluorometer of the present disclosure can include a variety of optical components, such as one or more detectors, excitation radiation sources, beam splitters lenses, mirrors, or the like, that form an optical train that directs excitation radiation through a single objective and/or that receives emission radiation through a single objective. In such embodiments, the objective can be configured as a macro-lens having a wide field of view. In alternative embodiments, a microfluorometer of the present disclosure can include a variety of optical components that directs excitation radiation through several objectives and/or that receives emission radiation through several objectives. Thus, an individual microfluorometer can include several optical trains that include several objectives. In embodiments that include several objectives per microfluorometer, the objectives can optionally be configured as an array of micro-lenses. Each objective among several in a particular microfluorometer (e.g. each micro-lens in an array of microlenses) can optionally be configured for independent focusing, whereby each objective can be moved in the z dimension independent of other objectives in the same microfluorometer. Alternatively or additionally, the several objectives can be configured for global focus such that they can all be moved together in the z dimension.

It will be understood that the various components of a read head that are set forth herein can be mixed and matched in various ways to achieve similar function to those exemplified herein. For example, as set forth in the previous paragraph, a read head can include several objectives and each of those objectives can be dedicated to a single microfluorometer or, alternatively, several of those objectives can be shared by a single microfluorometer. Similarly, and as set forth previously herein, each microfluorometer can include at least one dedicated excitation source or, alternatively, two or more microfluorometers can receive excitation radiation from a shared radiation source. Thus, there need not be a one to one correspondence between the number of microfluorometers in a particular read head and the number of components exemplified herein for any microfluorometer embodiment. Instead, one or more of the components exemplified herein as being useful in a microfluorometer can be shared by several microfluorometers in a particular read head.

A read head of the present disclosure is particularly useful for scanning methods and apparatus, for example, due to its relatively compact size and low mass which provides low inertia. Reduced inertia allows the read head to come to rest more quickly following movement, thereby allowing high resolution images to be obtained more rapidly than would be the case for a higher inertia read head for which residual movement of the read head would cause blurring and loss of resolution. Configurations for achieving movement of the read head will be set forth in further detail below. However, first it should be noted that the advantage of low inertia, is not intended to be a limitation or requirement for an apparatus or method set forth herein. Rather, a read head of the present disclosure can be maintained in a static position for all or part of a detection protocol. For example, a sequencing method, such as those using the fluidic and imaging steps set forth herein, can be carried out using a read head that is static during at least one and perhaps all of the cycles of the sequencing method. Similarly, the read head can be static during one or more steps of an inspection method set forth herein.

As a first example of a static read head embodiment, a read head can include a sufficient number of microfluorometers to detect or image a desired portion of a surface or other object. Thus, the read head need not move in the x or y dimensions. For example, several microfluorometers can be linearly arranged to capture image frames along the full length (or at least along the effective target length) of a flow cell channel or inspection apparatus channel. Similarly, using an appropriate packing arrangement of several rows of microfluorometers, such as those set forth herein, several flow cell channels (present in one or more flow cell), or several inspection apparatus channels, can be imaged along their full length (or at least along the effective target length). As set forth below herein, the image frames obtained for an individual channel can be, but need not be, contiguous.

As a second example of a static read head embodiment, a read head can remain at a fixed position with respect to the x and y dimensions while a substrate that is being detected by the read head is translated in the x and or y dimension. For example, an apparatus can be provided having a translation stage that is configured to present a substrate to the read head. The translation stage can move in a step-and-shoot or continuous motion to allow scanning of the substrate by the static read head. In particular embodiments, the substrate is a flow cell that can be affixed to the translation stage. Alternatively, the substrate can be an inspection apparatus.

In accordance with the above examples, relative motion between a scan head (or micro fluorometer) and a substrate can be achieved by physical movement of the scan head (or microfluorometer), physical movement of the substrate, or physical movement of both. It will be understood that the static read heads referred to in the first and second exemplary embodiments above need not be static with respect to movement in the z dimension. Rather the static read heads can include one or more microfluorometers having autofocus modules. Alternatively or additionally, the read heads can be moved as a whole in the z dimension, for example, to achieve global focus at least to a rough approximation.

Figure 3:
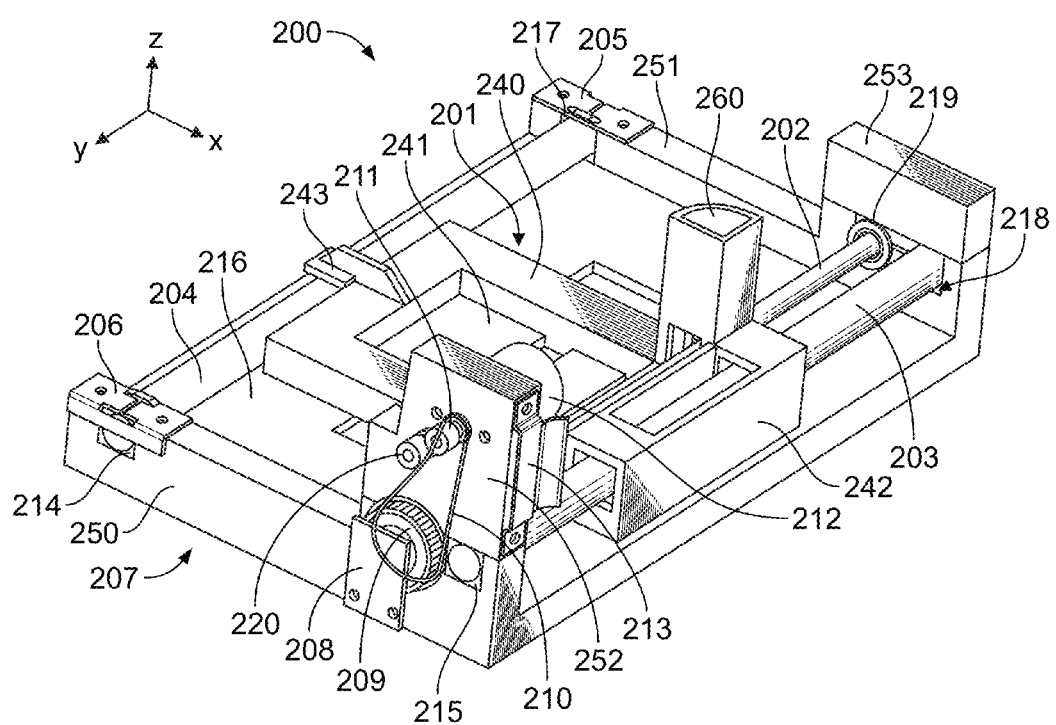
FIG. 3 shows a top perspective view of a Y-stage for a detection apparatus.
Figure 4:
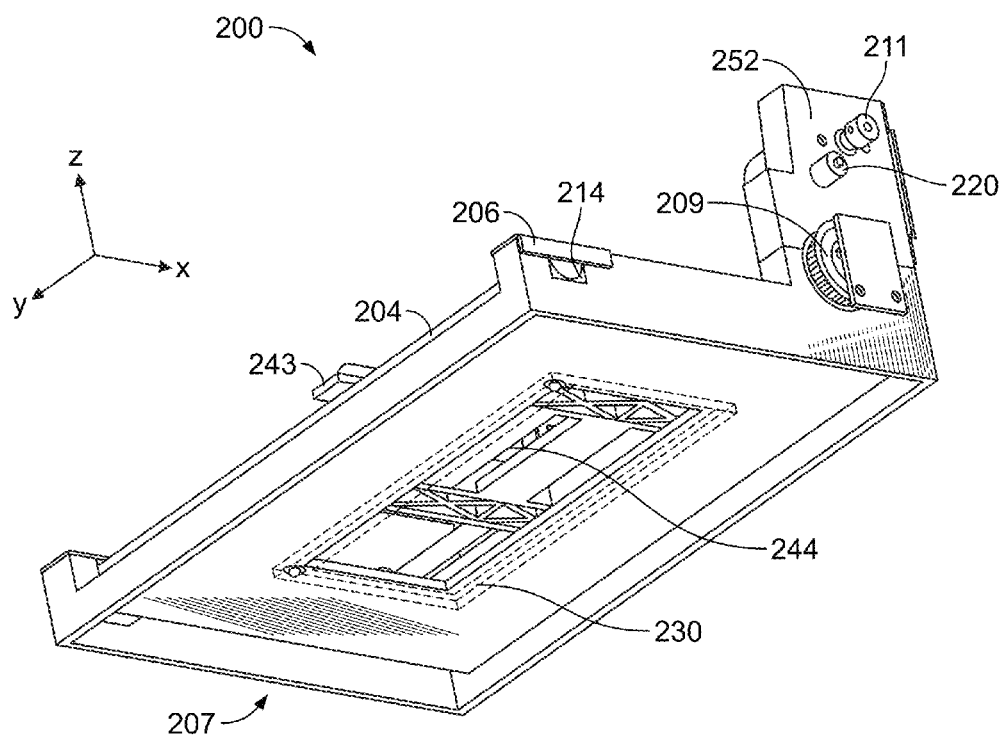
FIG. 4 shows a bottom perspective view of a Y stage for a detection apparatus.

Returning now to embodiments wherein a read head is translated, FIG. 3 and FIG. 4 show top and bottom views, respectively, of an exemplary y translation stage 200 for a read head. In this exemplary embodiment, the y stage is configured for translation in the y dimension but not in the x dimension. Thus, a read head carried by y translation stage 200 will be capable of movement in the y dimension and the read head or individual microfluorometers therein may be capable of movement in the z dimension (e.g. via autofocusing), but the read head will not be capable of movement in the x dimension. A read head can be affixed to carriage 201 having a base area 241 positioned to support the bottom side of the read head and a frame 240 configured to restrain the read head from side to side motion. The carriage 201 further includes a flange guide 243 and a collar guide 242. An opening 244 in base area 241 provides a window between a read head and substrate to be detected by the read head. The aforementioned components of the carriage 201 can form a monolithic structure.

The carriage is configured to move along a y stage frame 207 via a first shaft 203, along which the collar guide 242 runs and a second shaft 204 along which the flange guide 243 runs. The shafts are oriented along the y axis such that the carriage 201 is directed to slide back and forth along the y dimension via the guides. The first shaft 203 is held to the y stage frame 207 by insertion into datum 215 in a first side wall 250 and into datum 218 in a second sidewall 251. The first shaft 203 is clamped into datum 215 by support member 252 and clamped into datum 218 by support member 253. The second shaft 204 is held to the y stage frame 207 by insertion into datum 214 in a first side wall 250 and into datum 217 in a second sidewall 251. The first shaft 204 is clamped into datum 214 by shaft clamp 206 and clamped into datum 217 by shaft clamp 205.

Movement of carriage 201 is driven by rotation of lead screw 202 which is threaded through a lead nut 260 and which is affixed to the y stage frame 207 by insertion into a datum on the first side wall 250 and into a datum 219 in the second sidewall 251. The lead screw 202 is clamped in place by the same support members 252 and 253 that clamp the first shaft 203. The rotation of lead screw 202 is driven by motor 212 which is mounted to support member 252. An encoder 208 is configured to interact with the motor 212 via a belt 210 that interacts with rotor 209 on the encoder and rotor 211 on the motor 212. A belt tensioner 220 interacts with the belt 210.

An opening 230 passes through the floor 216 of y stage frame 207. The opening 230 is positioned to accommodate the trajectory of opening 244 in the base area 241 of the carriage 201 as it traverses the y stage frame. A read head is positioned in the carriage such that the objectives are directed through opening 244 and through opening 230 along a trajectory traversed by the carriage. Accordingly, the opening 230 accommodates imaging of an elongated area along the y axis via movement of a read head affixed to the carriage.

Figure 5:
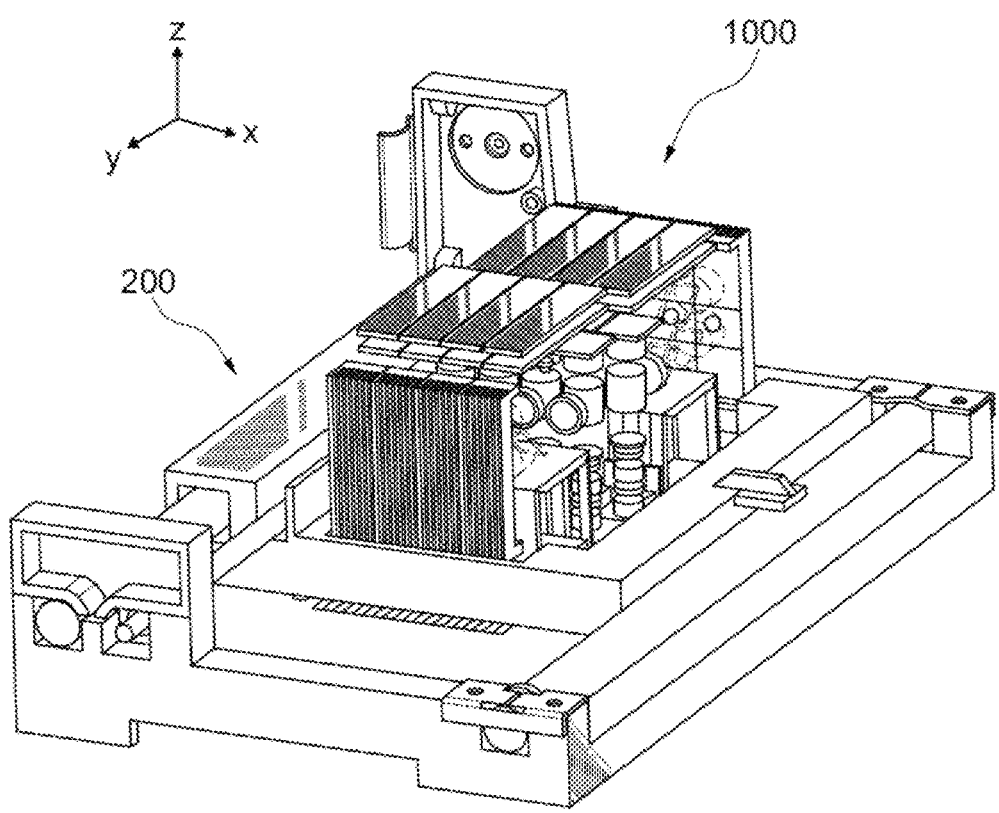
FIG. 5 shows a top perspective view of a Y-stage holding an arrangement of eight microfluorometers.

The structural and functional relationship between y translation stage 200 and read head 1000 is shown in FIG. 5. Alternative arrangements of microfluorometers, for example as set forth in US Pat. App. Pub. No. 2013/0260372 A1, can also be useful in combination with the inspection apparatus and inspection methods set forth herein.

A microfluorometer, or read head having several microfluorometers, can be positioned above a flow cell or inspection apparatus (with respect to gravity's arrow) as exemplified for several embodiments set forth herein. However, it is also possible to position a microfluorometer, or a read head, underneath a flow cell or inspection apparatus.

Accordingly a flow cell or inspection apparatus can be transparent on the top side, bottom side or both sides with respect to the wavelengths of excitation and emission radiation used. Indeed, in some embodiments it may be desirable to position microfluorometers on both sides of a flow cell or inspection apparatus, or alternatively, to position read heads on both sides of a flow cell or inspection apparatus. Other orientations with respect to gravity are also possible, including for example a side to side orientation between a flow cell and microfluorometer (or read head).

A microfluorometer or read head can be configured to detect the two opposing, inner surfaces of a flow cell (or inspection apparatus) from a single side of the flow cell (or inspection apparatus). For example, the microfluorometer or read head can employ an optical compensator that is inserted and removed to detect alternative surfaces of the flow cell or inspection apparatus. Exemplary methods and apparatus for detecting opposing inner surfaces of a channel such as the use of optical compensators are described in U.S. Pat. No. 8,039,817, which is incorporated herein by reference in its entirety. A compensator is optional, for example, depending upon the NA and/or optical resolution of the apparatus.

A microfluorometer used in an apparatus or method set forth herein can include an autofocus module. Accordingly, multiple microfluorometers that are present in a read head can each have a dedicated autofocus module. An autofocus module that is used in a microfluorometer can include a detector and an actuator, wherein the actuator is configured to alter the focus of the microfluorometer with respect to the common plane, and wherein the detector is configured to direct movement of the actuator. As such an autofocus module can include a dedicated detector that directs movement of the actuator. The dedicated detector can operate in a closed loop with the actuator without a need to communicate data outside of the microfluorometer or outside of the detection head in order to achieve automatic focusing. Alternatively or additionally, a detector outside of the autofocus module, such as the imaging detector that is used for wide-field imaging, can direct movement of the actuator. Thus, the same detector that is used for wide-field imaging and for outputting image data to a processing unit outside of the microfluorometer or read head can also be used to achieve automatic focusing.

In particular embodiments, autofocus modules for two or more microfluorometers in a read head can be configured to communicate with each other. For example, an autofocus module for a first microfluorometer of a read head can be configured to integrate data from an autofocus module for a second microfluorometer of the apparatus. In this way the autofocus module for the first microfluorometer can alter the focus of the first microfluorometer based on the perceived focus position of the first microfluorometer and the perceived focus position of the second microfluorometer. Thus, a detector for an autofocus module can be configured in a way that it is dedicated to focusing generally across a read head while not being configured for analytical image acquisition. Information from two different autofocus modules can be useful in determining tip-tilt of the read head. Undesirable tip-tilt can be corrected by compensatory actuation of one or more microfluorometers based on the tip-tilt information.

Figure 6A:
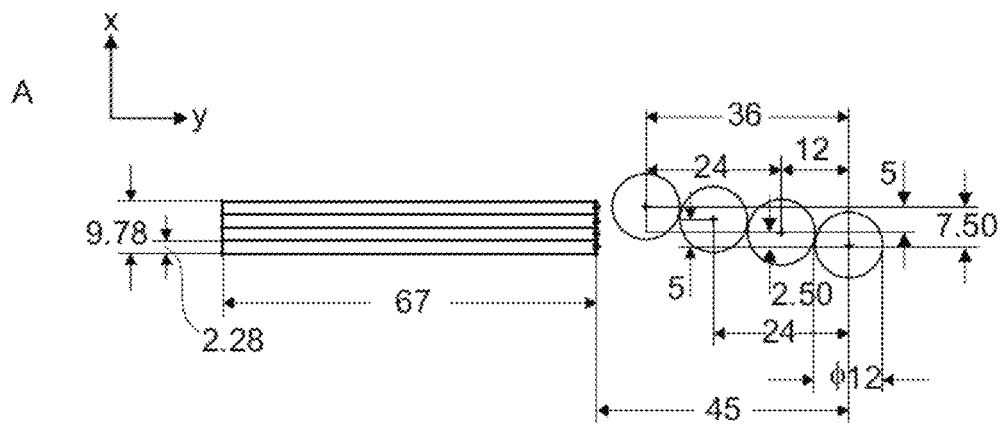
FIG. 6A shows an arrangement of four microfluorometers in relation to a flow cell having four channels.

A read head can include two or more microfluorometers, for example, attached to a carriage. For embodiments that utilize a multichannel flow cell (or inspection apparatus), the read head can include a number of microfluorometers that correspond to the number of channels in the flow cell (or inspection apparatus). More than one microfluorometer per channel can be present. In particular embodiments, a read head can provide a single microfluorometer channel. In the exemplary arrangement shown in FIG. 6A, the flow cell has four channels and the read head has four microfluorometers. The figure shows a top plan view of the flow cell and objectives of the microfluorometers. For ease of demonstration components of the microfluorometers other than the objectives are not shown; however, those components can be positioned to achieve a compact design, for example, along the lines exemplified elsewhere herein. As shown in FIG. 6A, the four objectives can be arranged in a linear relationship such that the objectives are closely packed and an imaginary straight line passes through the center point of each objective. The imaginary line can be offset at an angle with respect to the y dimension, the y dimension corresponding to the longest dimension of the flow cell (or direction of scan). The angle can be between 0° and 90° in the x-y quadrant and can be selected to accommodate the spacing of the channels in the flow cell (and the spacing of the objectives in the read head). FIG. 6A shows a relatively low angle of offset for a line passing through closely packed objectives which accommodates relatively closely packed channels. A higher angle of offset can be used to accommodate channels that are separated by greater distances from each other or objectives that are less closely packed.

Figure 6B:
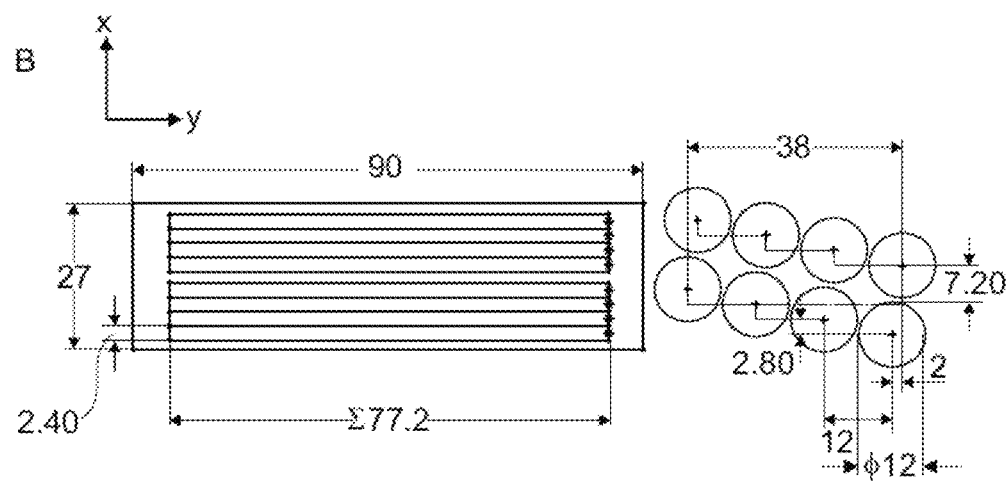
FIG. 6B shows an arrangement of eight microfluorometers in relation to a flow cell having eight channels.

FIG. 6B shows an arrangement of multiple objectives in two lines. Here the flow cell includes eight channels and the read head has eight microfluorometers. The overall packing of the objectives in the two lines is approximately rectilinear. The arrangement accommodates closely packed objectives and two sets of closely packed channels (i.e. a first set of four closely packed channels and a second set of four closely packed channels). In this example, the two sets of closely packed channels are separated by a larger spacing than the spacing that separates individual channels in each set of four. It will be understood that the overall packing of the objectives in the two lines can be offset from rectilinear to accommodate different channel arrangements. Furthermore, as set forth in regard to a single line of objectives, the offset angle of the imaginary line running through the centers of both lines of objectives can be altered and/or the distance between objectives can be altered to accommodate different channel arrangements.

As demonstrated by the examples above, each objective in a read head can be positioned to image at least a portion of an individual channel (of a flow cell or inspection apparatus). Each objective can be positioned to image one and only one channel of a flow cell or inspection apparatus having several channels. An individual objective can be positioned to image a portion of one and only one channel, for example, when located at a particular y-stage position. Scanning in the y dimension can allow all or part of the channel to be imaged through the objective. In some cases, for example when the field diameter of the objective (or other limiting optical components of a microfluorometer) is less than the width of the channel, the objective can also be scanned in the x dimension to image all or part of the channel. Multiple objectives and their respective microfluorometers can be positioned such that several of the objectives are positioned to each obtain images for at least a portion of one and only one channel. Of course movement of a read head containing the multiple objectives and their respective microfluorometers can occur in the y and/or x direction to image all or part of each respective channel. These particular configurations are useful for multichannel flow cells or multichannel inspection apparatus. However, it will be understood that the configurations and underlying principles set forth above can be applied to an appropriate arrangement of several individual flow cells or inspection apparatus, each having only a single channel. Furthermore, as is the case generally for the methods and apparatus set forth herein, the arrangements can be applied to substrates other than flow cells and inspection apparatus.

As exemplified above a carriage can be configured to move a read head, for example, in a scanning operation. Alternatively or additionally, a carriage can be configured to prevent relative movement between individual microfluorometers of a read head in the x and y dimensions. A carriage need not provide this function, for example if the read head includes other structure elements that prevent relative transverse motion between individual microfluorometers, For example, a read head may be formed from a co-molded assembly (e.g. a monolithic assembly). The co-molded assembly can in turn be affixed to a carriage. Nevertheless, in some embodiments, the carriage may play at least an auxiliary role in preventing relative transverse motion between individual microfluorometers of a read head. Furthermore it will be understood that a read head that is formed from a co-molded assembly can be used for embodiments that do not employ a carriage.

A y stage that is used in a method or apparatus set forth herein can be configured to scan via a discontinuous or continuous motion. Discontinuous scanning, often referred to as step-and-shoot scanning, generally involves incremental movement of a microfluorometer or scan head in the y (or x) direction and detection (e.g. image acquisition) between movements, while the microfluorometer or scan head is in a temporarily static state. Continuous scanning on the other hand generally involves detection or image acquisition while the microfluorometer or scan head is moving. In a particular embodiment continuous scanning can be carried out in time delay integration (TDI) mode. Accordingly, signal obtained by pixel elements along the scan dimension can be collected in a common bin and read out as a single value. TDI mode can provide advantages of increased signal processing rate and increased accuracy. Exemplary optical arrangements that can be included in a microfluorometer or read head to accommodate TDI mode detection are described, for example, in U.S. Pat. No. 7,329,860, which is incorporated herein by reference.

A readout printed circuit board (PCB) can be present in a read head (see, for example, PCB 1701 and 1702 in FIG. 2) and can be connected to a main PCB that is typically contained within the detection apparatus housing. In alternative embodiments the main PCB can be located exterior to the instrument. Data can be communicated to and from the readout PCB and/or main PCB as set forth in US Pat. App. Pub. No. 2013/0260372 A1. In particular embodiments, the main PCB can also be connected to an exterior primary analysis personal computer (PC). In some embodiments the primary analysis computer can be located within the housing of the detection apparatus. However, placing the primary analysis computer off-instrument allows for interchangeable use of a variety of computers to be used for different applications, convenient maintenance of the primary analysis computer by replacement without having to interrupt the activity of the detection apparatus and small footprint for the detection apparatus. Any of a variety of computers, can be used including, for example, a desktop computer, laptop computer, or server containing a processor in operational communication with accessible memory and instructions for implementation of the computer implemented methods described herein. The main PCB can also be connected to a user interface.

Other imaging modules that can be evaluated using an inspection apparatus of the present disclosure include, but are not limited to, those in a HiSeq® platform, MiSeq® platform, HiScan® platform or those set forth in PCT Pub. No. WO 07/123744; US Pat App. Pub. Nos. 2012/0270305 A1; 2013/0023422 A1; and 2013/0260372 A1; and U.S. Pat. Nos. 5,528,050; 5,719,391; 8, 158,926 and 8,241,573, each of which is incorporated herein by reference Apparatus for Alignment and Validation of an Imaging Module The following description and related drawings set forth one or more embodiments of inspection apparatus and methods. In some embodiments, the inspection apparatus can be used for alignment or validation of the imaging modules exemplified above. Furthermore, the inspection methods can be carried out for validation and alignment of the exemplified imaging modules or optical components thereof. It will be understood, that various modifications may be made to the inspection apparatus, inspection methods and/or the imaging modules that they are used with. One or more of the optical characteristics of an imaging apparatus, including but not limited to those set forth above, can be evaluated using an inspection apparatus or method set forth herein. Furthermore, an inspection apparatus can be used in combination with an analytical substrate (e.g. a flow cell). In some embodiments, methods can be carried out to include steps of an inspection method and steps of an analytical method (e.g. a nucleic acid sequencing method).

An exemplary inspection apparatus is referred to herein as "Ubertarget apparatus". The Ubertarget apparatus is an optical alignment tool that can be used for sequencer Imaging Module tests. The composition, manufacture and use of the Ubertarget apparatus exemplified below can be extended to other inspection devices as well.

In some embodiments, the Ubertarget apparatus can be used (1) in a fully-integrated nucleic acid sequencer system (such as a NextSeq® sequencer system (Illumina, Inc., San Diego)), (2) at any point in the manufacture process of a sequencer after the imaging module (IM) is installed, (3) as a field service tool for installation or service of a sequencer system, (4) in quality control fixtures for evaluating manufacture of various components of the NextSeq® sequencer or (5) in a stand-alone camera module test station.

The Ubertarget apparatus, for example, when used to align or validate a sequencer, can be illuminated with a light source that is part of the sequencer, such as a green and/or red LED in the camera modules (also referred to as "microfluorometers") of a NextSeq® sequencer system (Illumina, Inc., San Diego). In this example, the LED illumination will excite a fluorescing dye in the Ubertarget apparatus. It is also possible to use a light source that is extrinsic to the sequencer, such as a backlight that is positioned to shine up through the Ubertarget apparatus when the Ubertarget apparatus is located in the sequencer instrument.

Figure 7A:
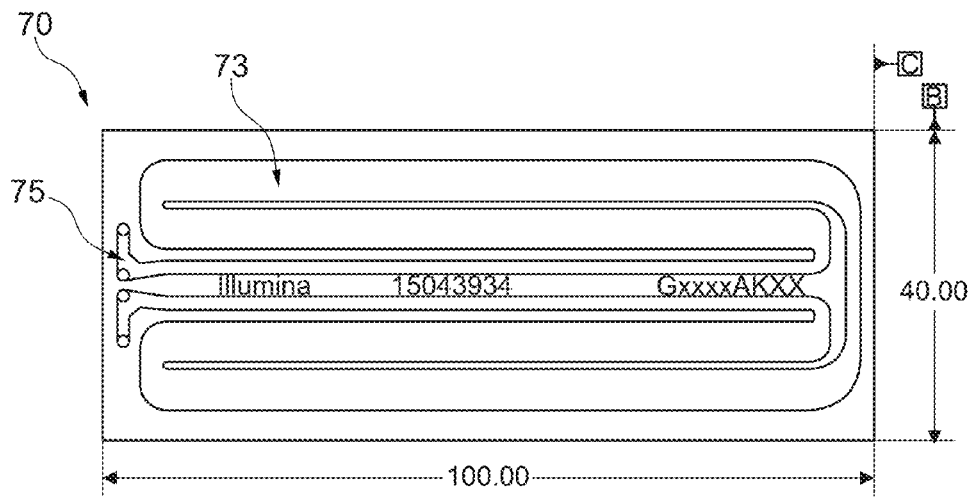
FIG. 7A shows a top view of an Ubertarget apparatus.
Figure 7B:
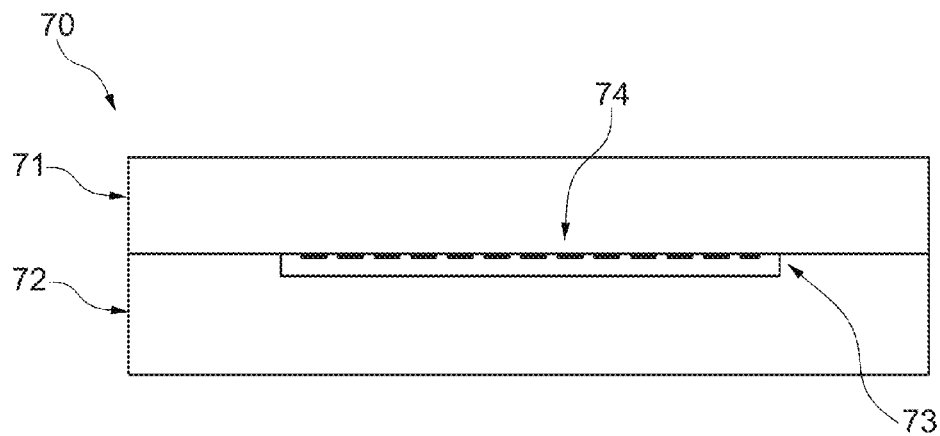
FIG. 7B shows a side view of a channel of an Ubertarget apparatus.

Diagrams of the Ubertarget apparatus 70 are shown in FIG. 7A and FIG. 7B. As shown in the top view of FIG. 7A, the Ubertarget apparatus 70, which is designed for use in a NextSeq® Sequencer, has dimensions (100 mm×40 mm) that are similar to the flow cell used in the sequencer. Thus, the Ubertarget apparatus 70 can be readily positioned on the stage of the sequencer for alignment and validation procedures. The fluidic channel 73 of the Ubertarget apparatus 70 has overall dimensions that are similar those of the channels in the flow cell. As demonstrated by this example, it is beneficial for an inspection apparatus (e.g. Ubertarget apparatus) to have lanes located at the same relative position as the channels of an analytical apparatus (e.g. flow cell) that are optically addressed by the imaging module (e.g. NextSeq® Sequencer) during use of the analytical apparatus. Of course small differences in channel size and shape can be accommodated, and need not result in significant reduction in the diagnostic capability of the inspection apparatus. For example, as set forth in further detail below, the portion of the Ubertarget channel 75 having fluid entry and exit ports differs from the portion of the flow cell that has entry and exit ports. However, these differences do not directly impact the ability of the Ubertarget apparatus to be used for alignment and validation of the NextSeq® Sequencer optical components along the entirety of the detected portion of the flow cell because the inlet and outlet regions are not addressed by the imaging module of the NextSeq® Sequencer. The Ubertarget apparatus can also include identifying indicia such as a serial number, part number or barcode.

As evident from the side view of the Ubertarget apparatus 70 in FIG. 7B, the thickness of the top glass 71 (700 μη+/−10μη) and bottom glass 72 (800 μη+/−15 μη) is similar to the respective thickness of these sides of the NextSeq® flow cell. The thickness of the channel opening 73 in the z dimension (100 μη+/−10μη) is also similar to that found in the flow cell. Generally, it is beneficial for the dimensions of an inspection apparatus, through which optical inspection occurs, to be similar to those dimensions of the analytical apparatus through which analytical detection occurs. However, if desired or necessary, the dimensions of one or more of these components can differ between the inspection apparatus and relevant analytical apparatus. In this case, theoretical or a priori parameters can be used to correlate measures obtained from the inspection apparatus and analytical apparatus. The Ubertarget apparatus can also include at least one tile having a pattern of metal pads (e.g. 50 nm thick chrome pads) on the bottom side of the top glass. The metal pads can be used for optical analysis as set forth in further detail below.

The entirety of an inspection apparatus' inner surface can contain metal pads. However, the entire surface need not contain pads. Rather one or more tiles (or other portions) on the surface that is to be imaged can lack metal pads. Tiles with no metal pads provide a uniform light across the field of view that enable fixed pattern noise calibration or flat field correction, for example, using methods exemplified for an Ubertarget apparatus and NextSeq® sequencer herein below. Such corrections can be determined for several excitation sources individually. Alternatively or additionally, one or more portions of an inspection apparatus' inner surface can contain a fiducial.

Figure 8:
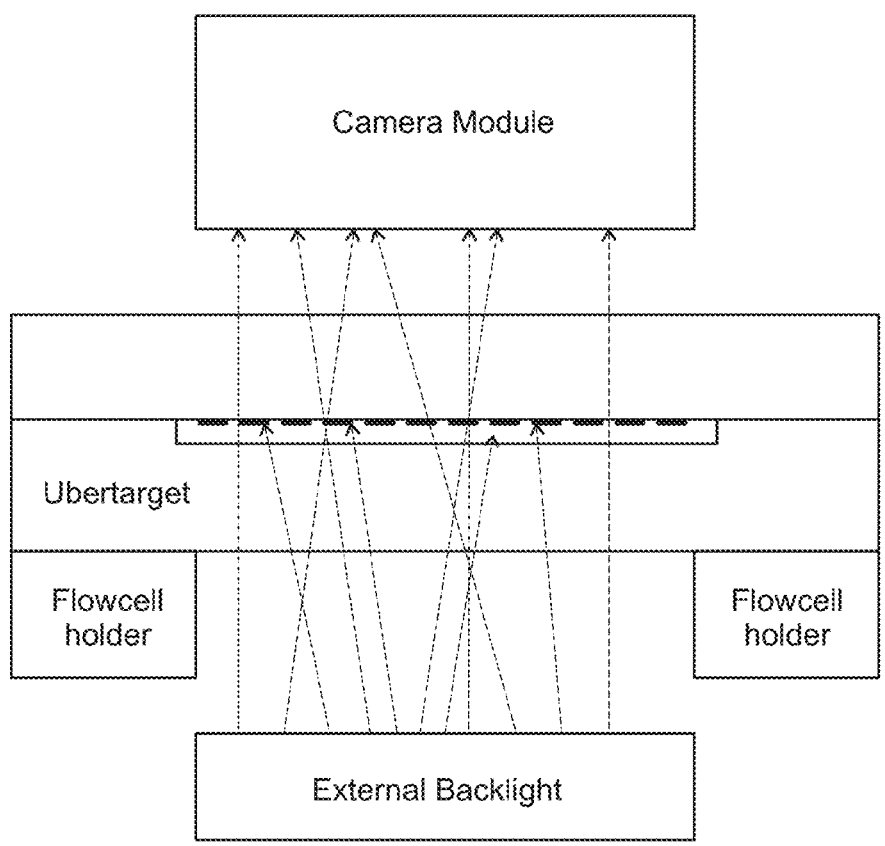
FIG. 8 shows a diagram of a back illumination scheme for an inspection apparatus used in an inspection method.

An inspection method can use a back illumination of an inspection apparatus as diagrammed in FIG. 8. In the example the Ubertarget apparatus is placed on the flow cell holder of a NextSeq® imaging module and an external backlight illuminates the underside of the Ubertarget apparatus. White light from a lamp can be used. The light passes through the lower glass, through the channel opening and to the lower surface of the upper glass. At this surface the light will either be blocked by the metal pads or it will transmit through the upper glass to the camera module of the instrument that is under analysis. The metal pads appear as dark shadows in a field of light detected by the camera. The optical components can be focused on the metal pads and accuracy of focus can be determined from the sharpness of the shadows produced by the pads.

Figure 9:
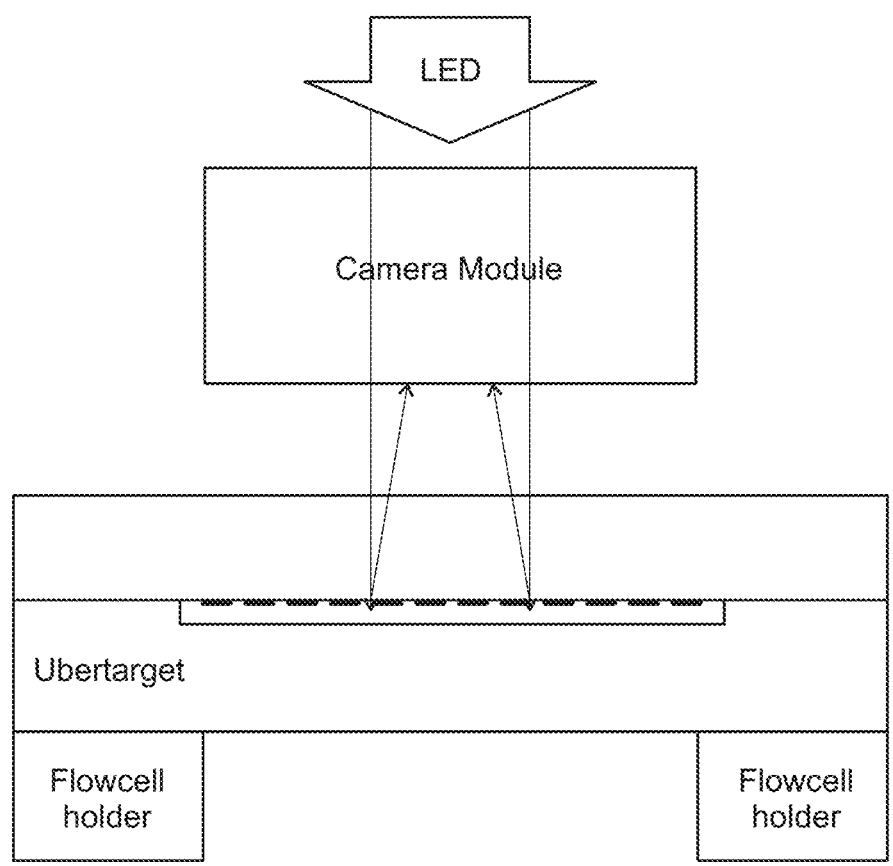
FIG. 9 shows a diagram of an epifluorescence scheme for an inspection apparatus used in an inspection method.

An alternative inspection method is diagrammed in FIG. 9 where an LED of the NextSeq® imaging module is used instead of an external backlight. In this case, the channel opening of the Ubertarget apparatus is filled with a fluorescent dye that is excited by the LED to produce a fluorescent emission. The channel opening can be filled with a mixture of more than one fluorescent dye. For example, the Ubertarget apparatus can be filled with a first dye that is excited by a red LED and a second dye that is excited by a green LED. This will allow both the red and green channels of the NextSeq® imaging module to be evaluated. As shown by the diagram of FIG. 9, the Ubertaget can be placed for epifluorescence detection such that excitation light impinges on the top side of the top glass and transmits to the lower surface of the top glass. LED light can pass into the channel opening to excite the fluorescent dye but LED light that hits the metal pads is prevented from exciting dye. Emission from the dye passes back through the upper glass and to the camera where it is detected. Again, the resulting image will appear as a pattern of shadows cast by the metal pads in a field of fluorescent emission light. The optical components can be focused on the metal pads and focus can be determined from the sharpness of the shadows produced by the pads.

In particular embodiments, the Ubertarget apparatus can be filled with Rhodamine 590 dye and Oxazine 750 dye. The Rhodamine 590 dye can be excited by the green LED at 532 nm and emission can be collected through a 550-610 nm bandpass filter. The Oxazine 750 dye can be excited by the red LED at 660 nm and emission can be collected through a 695-730 nm bandpass filter. These conditions were found to separate red and green emission signals with no appreciable cross talk.

Dye material can be introduced to an Ubertarget channel as follows. Glycol is flushed through the channel of the Ubertarget apparatus to clean out the channel. The volume of glycol flushed through is 25 mL which is 100 times the volume of the channel. The glycol is pumped at a rate of 150 $\mu E/\eta \mu \eta$. Dye solution is then pumped into the lane. The dye solution contains 1.46 µg Exciton Rhodamine 590 (Green Dye) per mL of glycol and 13 µg Exciton Oxazine 750 (Red dye) per mL of glycol. A volume of 1.25 mL of the dye mix is pumped at a rate of 150 $\mu E/\eta \mu \eta$. The channel openings are then sealed and the Ubertarget apparatus is ready for use after the sealant has cured for 24 hours. A useful sealant is white silicone (kitchen and bath) from DAP (Baltimore, Md.).

The mixture of Rhodamine 590 and Oxazine 750 was found to be very photostable. Photobleaching experiments showed that an Ubertarget apparatus used to qualify imaging modules experiences only a 3% drop in the fluorescence of the red and green dyes. Each Imaging Module qualification consisted of: (1) acquiring 300 images of the open lane in each color for Flat Field Correction and Fixed Pattern Noise, (2) acquiring 90 images of the fiducials for determining best-focus down lanes, (3) acquiring 120 images of the fiducials for XY position tests of the XY stage and (4) acquiring 30 images of the image quality tile for optical alignment measurements. The dyes are able to diffuse throughout the channel so that there is no localized bleaching. Thus, when multiple cameras are used, each of the cameras is expected to view the same apparent intensity of dye. Accordingly, the dye solution in the Ubertarget apparatus provides a useful tool to measure the relative LED power at each region of the detection field combined with emission transmission efficiency. The relatively high photostability of the dyes can also allow for LED calibration using the Ubertarget apparatus.

The mixture of Rhodamine 590 and Oxazine 750 was found to be very heat stable. Zero degradation in intensity of the dyes was observed after baking at 65 degrees C. for 5 days. Heat stability of the dyes indicated that the Ubertarget apparatus is robust through the course of imaging module optical alignment measurements at normal operating temperature conditions for a NextSeq® sequencer (60 degrees at the flowcell holder).

Although Rhodamine 590 and Oxazine 720 provide particular advantages, other fluorescent species can be used. Examples of useful fluorescent species include those having the following moieties: umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue™, Texas Red™, dichlorotriazinylamine fluorescein, dansyl chloride, phycoerythrin, fluorescent lanthanide complexes such as those including Europium and Terbium, Cy3, Cy5, nanocrystals, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland. Luminescent materials can also be useful such as luminal.

Figure 10:
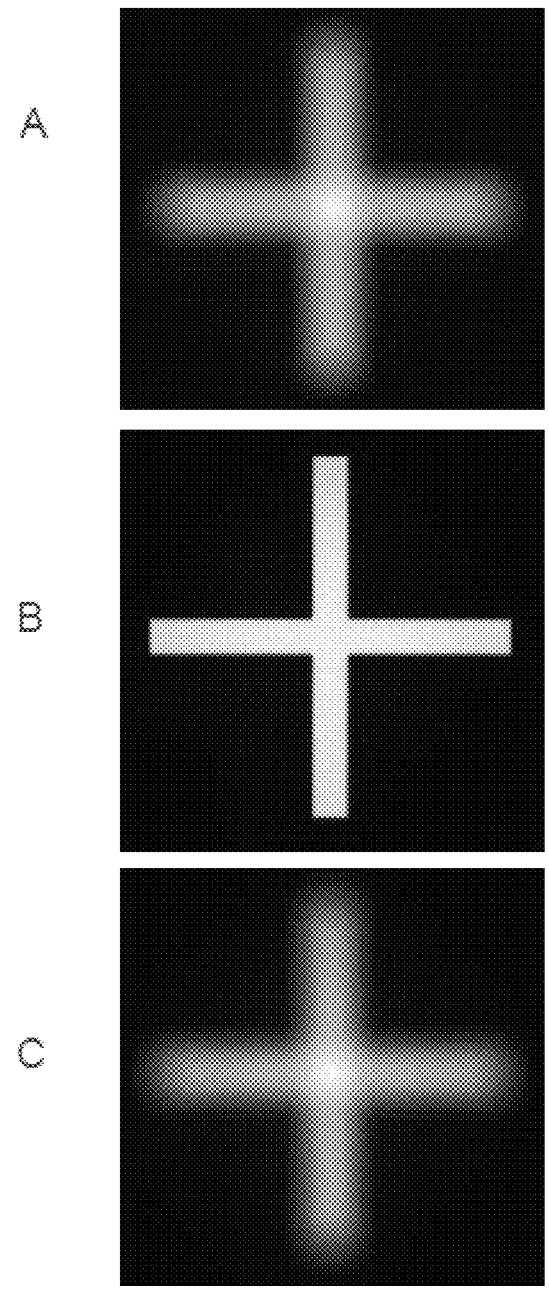
FIG. 10 shows images obtained from a NextSeq® imaging module focused above the metal layer of an Ubertarget apparatus (Panel A), at the metal layer (Panel B) and below the metal layer (Panel C).

FIG. 10 shows fiducial images obtained from a NextSeq® imaging module focused above the metal layer of an Ubertarget apparatus (Panel A), at the metal layer (Panel B) and below the metal layer (Panel C). As demonstrated by the images the metal regions appear dark and the fiducial areas with no metal appear white (e.g. shaped like a "+" in the images). The edges of the metal appear sharp in Panel B due to the camera being in focus with the pads as opposed to the blurry edges of the metal in Panels A and C where the camera is out of focus. The "+" shaped object is relatively large which provides the advantage of allowing it to be visible even when it is far out of focus.

Figure 11A:
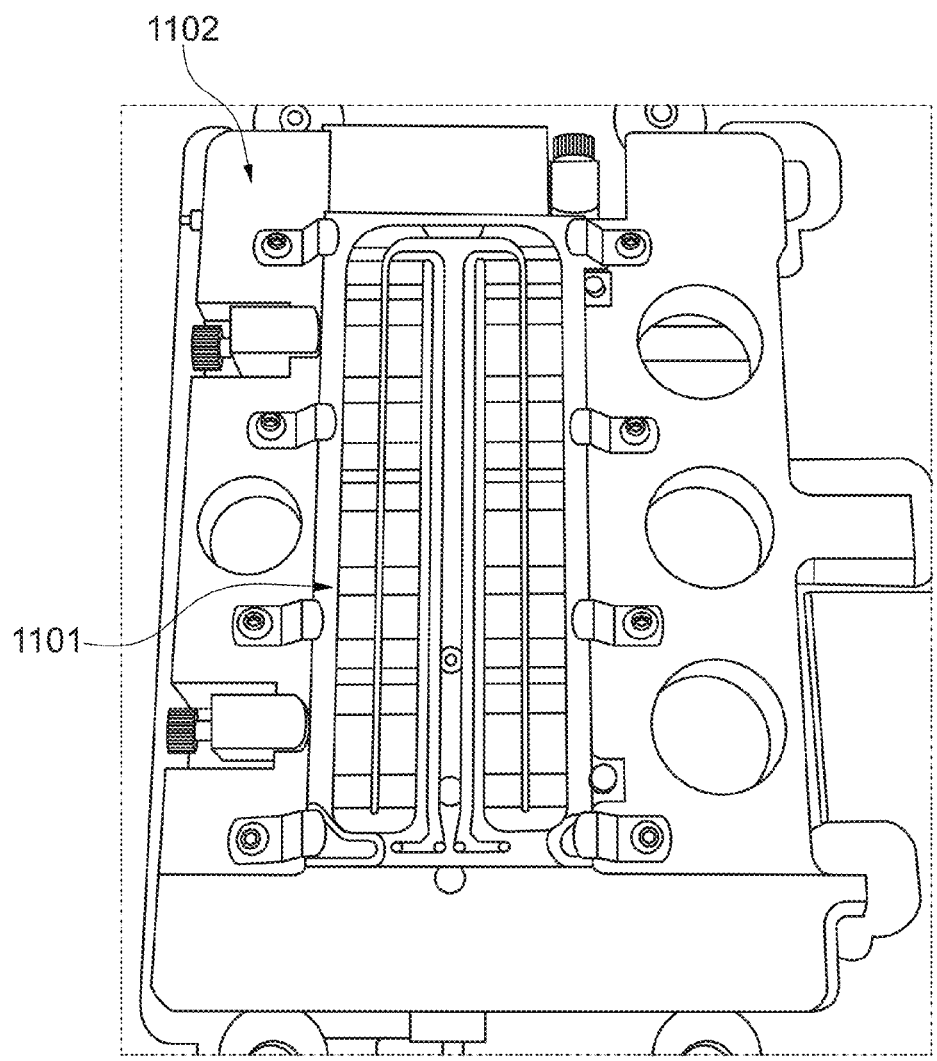
FIGS. 11A-B shows photographs of an Ubertarget in a quality control fixture (Panel A) and in a cartridge fitted to a NextSeq® sequencer (Panel B).
Figure 11B:
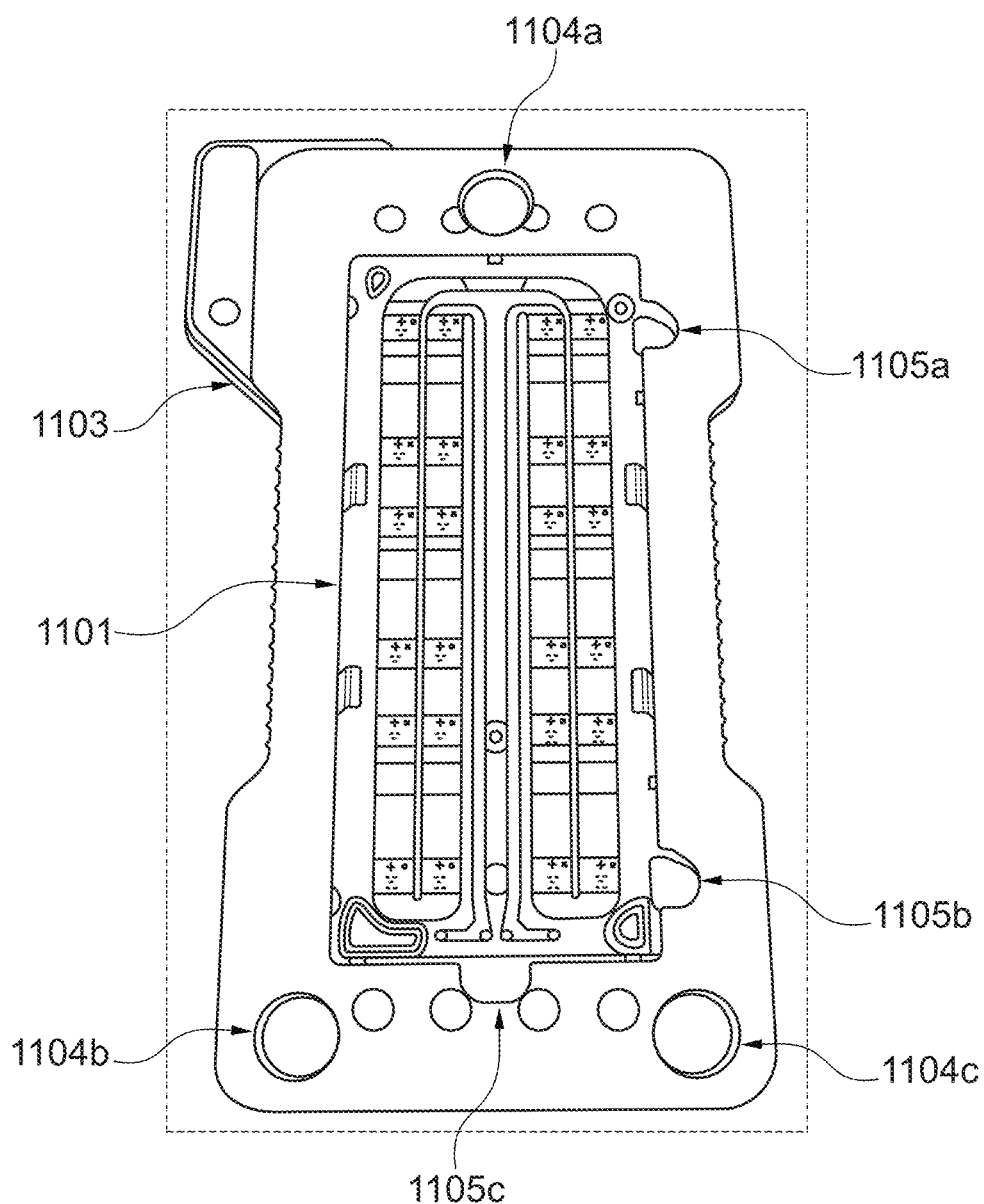

FIGS. 11A-B shows photographs of an Ubertarget 1101 in a quality control fixture 1102 (Panel A) and in a cartridge 1103 fitted for a NextSeq® sequencer (Panel B). The cartridge 1103 has the same dimensions as a cartridge used for a NextSeq® flow cell. The cartridge 1103 includes contact points 1 104a, 1 104b and 1104c for z-reference datum pins on the underside of the xy stage of the NextSeq® sequencer. This provides mechanical reference for z, theta-x and theta-y coordinates. Ubertarget 1 101 floats in cartridge 1 103, but once cartridge 1 103 is placed on the heater plate of the NextSeq® sequencer, 3 dowel pins pass through openings 1105a, 1 105b and 1 105c and contact the edge of Ubertarget 1 101 to seat Ubertarget 1 101 on the imaging module. This provides mechanical reference for x, y and theta z.

The present disclosure provides an inspection apparatus that avoids problems of channel dryout and bubble formation. As exemplified above, the Ubertarget apparatus uses glycol which does not make bubbles easily. Other high viscosity solvents can produce this advantage as well. In addition to high viscosity it can be beneficial to use a solvent having a high boiling point. For example, glycol in addition to being highly viscous has a high boiling point (190° C.) which minimizes evaporation at the temperatures at which the Ubertarget apparatus is stored, transported and used. Furthermore, channel sealing can be achieved using a highly compliant silicone RTV (room temperature vulcanization) injected into the ingress and egress ports of the channel. Silicone is particularly useful because it is compatible with the Ubertarget apparatus: (1) resulting in less than 250 nm of glass deformation upon curing, (2) resisting degradation when submerged in glycol (e.g. for over 1 month in a shelf life test), (3) being capable of curing to form a seal when in contact with glycol, (4) being inert to dye molecules, and (5) being inexpensive, easy to dispense, and providing a visual indication of seal quality.

Figure 12A:
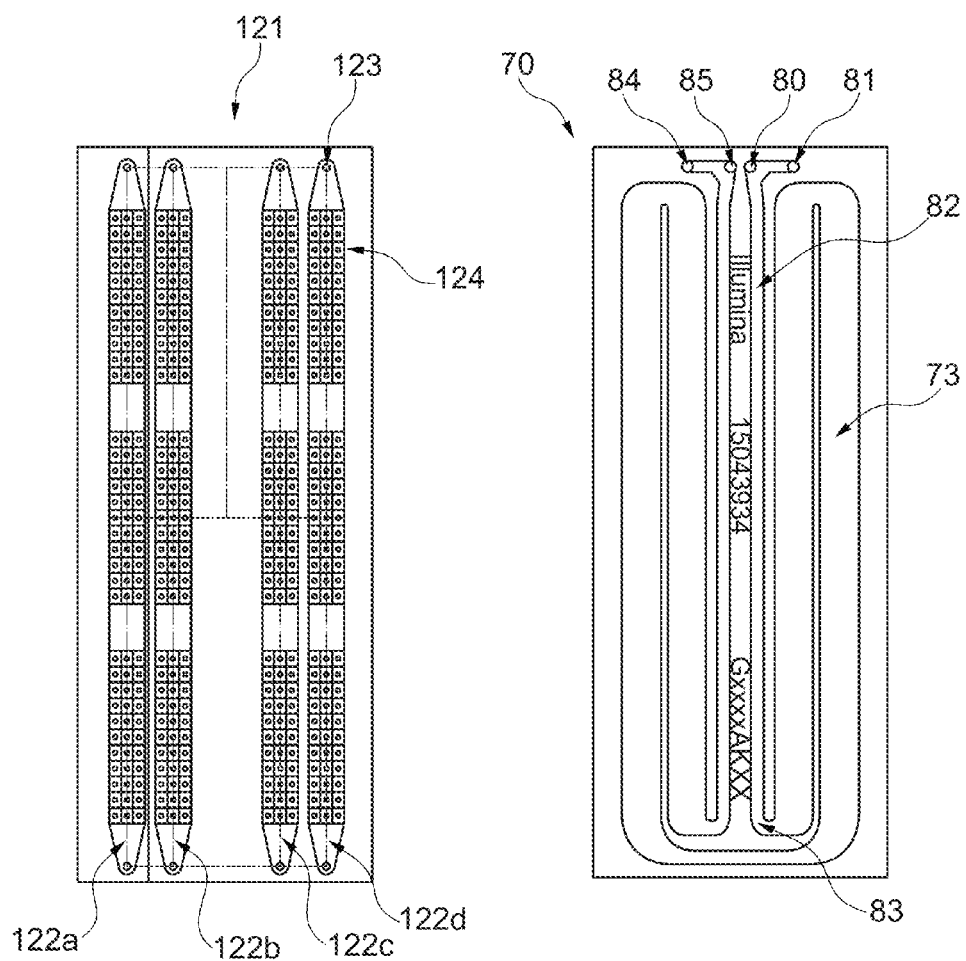
FIG. 12A shows an inspection apparatus having multiple channels (left) and an inspection apparatus having a single channel with multiple lanes.

In particular embodiments, an inspection apparatus can include structural elements that minimize or prevent channel dryout and bubble formation. For example, Ubertarget apparatus 70 contains a sacrificial channel region as indicated by the diagram of FIG. 12A. On the left is an inspection apparatus 121 having four separate channels 122a-122d in the same footprint as a NextSeq® flow cell. Taking channel 122d as an example, inlet 123 is relatively close to the first set of detection tiles 124. A bubble that starts growing at inlet 123 will encroach upon tiles 124 after growing only a few millimeters in diameter. In contrast, Ubertarget apparatus 70 contains an extended sacrificial lane 82 that forms an ingress lane between the inlet port 80 and the first detection lane of channel 73. The first detection lane is the relatively wide region having a footprint and location that correlates with channel 122c of inspection apparatus 121. In the example shown, the sacrificial region is about 100 mm long such that a bubble forming at inlet 80 would need to expand to a large volume prior to having an adverse impact on a procedure using Ubertarget apparatus 70. A similar sacrificial region forms an egress lane between outlet 85 and the fourth detection lane of channel 73 (i.e. the lane corresponding to channel 122b of apparatus 121). This prevents bubble encroachment from the other side of the channel 73. As shown in the diagram, Ubertarget apparatus 70 contains one channel in which wide sections, that correlate with the imaging windows of channels 122a-122d of flow cell 121, are connected in a serpentine fashion. The single channel configuration provides ease of filling the Ubertarget apparatus 70 and uniformity of dye solution across all four of the regions that correlate with channels 122a- 122d of flow cell 121.

An additional structural element of Ubertarget apparatus 70 that minimizes or prevents channel dry out and bubble formation is the presence of a pressure relief port 81 near the inlet port 80. The pressure relief port 81 prevents damage to a seal at inlet port 80 when the outlet port 85 is sealed (i.e. damage can occur due to introduction of the seal fluid into the closed system that has been produced due to the seal at the opposite end of the channel). Damage to the seals can be prevented in Ubertarget apparatus 70 by using the following technique. After filling channel 73 with dye solution, a removable tape or other seal is placed over outlet port 85 and outlet pressure release port 84. Then sealant is injected into inlet port 80 and allowed to flow until flowing out of inlet pressure relief port 81. Then the tape or other removable seal is placed over inlet port 80 and inlet pressure relief port 81. Once the inlet is sealed in this way sealant can be injected into outlet port 85 and allowed to flow until flowing out of outlet pressure relief port 84. In this way the pressure relief ports provide a vent to avoid damage to the seal between ports 80 and 81, thereby preventing unwanted bubble formation and drying during later use.

An inspection apparatus need not include pressure relief ports. Furthermore, the channel need not be sealed using a seal fluid (e.g. silicone). For example, in some embodiments there is a single ingress port and a single egress port. The ports can be sealed using a flexible tape such as Kapton tape. The tape has an advantageous property of acting like a diaphragm, where it maintains a seal, but can expand away from the port or contract into the port depending on the internal lane pressure (e.g. pressure changes typically due to temperature changes). The tape also has the advantage of allowing refilling or manual venting of the Ubertarget apparatus, for example, if bubbles form in the lane over time.

Unwanted bubble formation can also be avoided by degassing fluids that are loaded into the Ubertarget apparatus. For example, temperature changes may cause bubbles to form in the middle of the lanes. This is caused by dissolved gas in the fluid coming out of solution and making a permanent bubble. Bubble formation has been avoided by putting glycol-dye solution in a vacuum chamber and pulling air out of the solution immediately before pumping the solution into the Ubertarget apparatus.

In particular embodiments, an inspection apparatus will have a high degree of flatness. It is particularly advantageous to have a high degree of flatness for surfaces that are to be imaged, such as the surfaces of the top glass and bottom glass of an Ubertarget apparatus that face the inside of the channel. An Ubertarget apparatus having a flatness variance of less than 12 $\mu m$ across the length of the detection area is particularly useful. Ubertarget apparatus having a variance of +/−3 $\mu m$ have been found to be particularly useful.

Figure 12B:
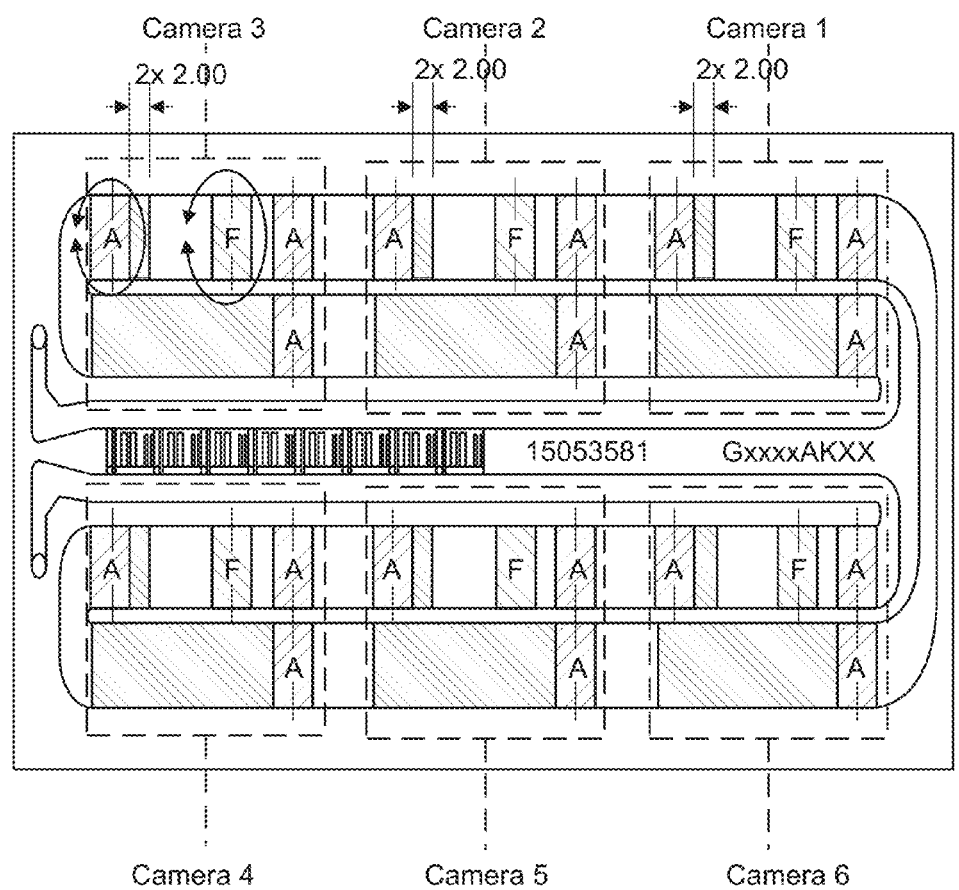
FIG. 12B shows the location of printed patterns on an Ubertarget apparatus along with the image areas for the 6 cameras of a NextSeq® imaging module.
Figure 12C:
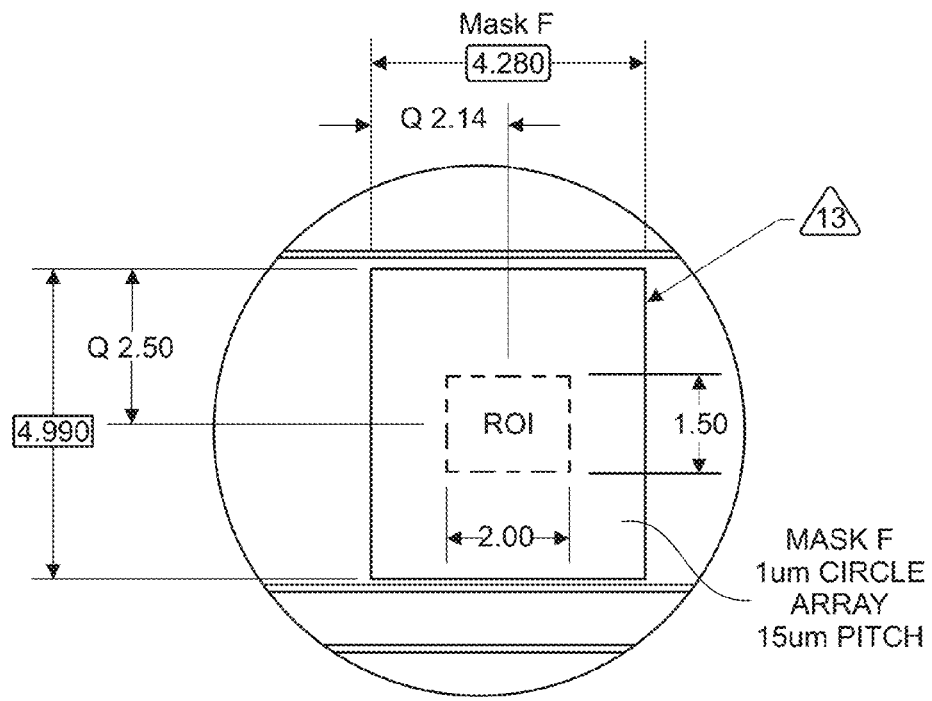
FIG. 12C shows further detail for the Mask F and Mask A regions of the Ubertarget apparatus shown in FIG. 12B.
Figure 12C:
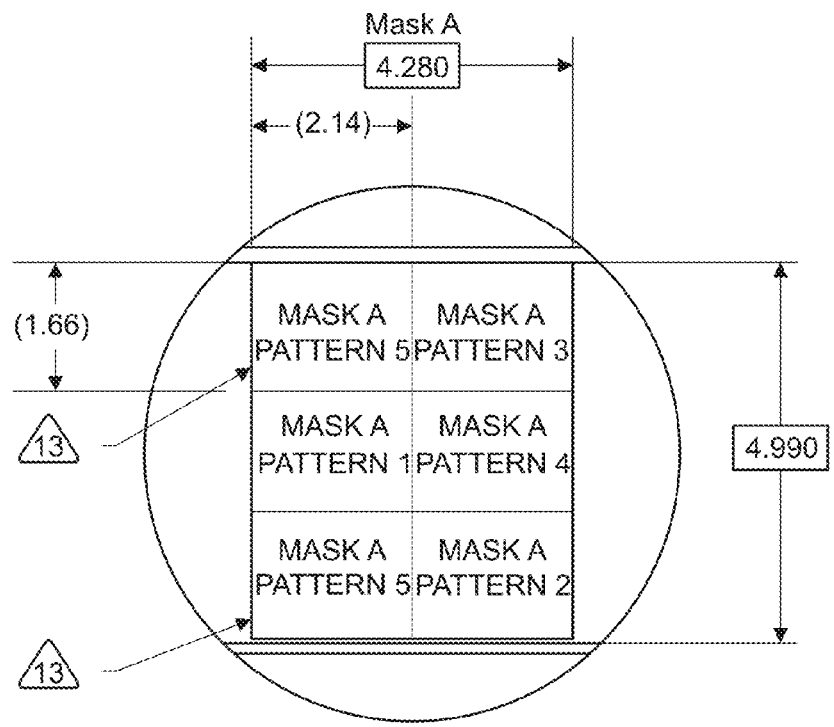

FIG. 12B shows the location of printed patterns on an Ubertarget apparatus along with the image areas for the 6 cameras of a NextSeq® imaging module. The same pattern is printed for each of the 6 cameras. Various regions of each image area are indicated in the Figure. For example, the regions shaded with alternating solid and dashed lines are transparent, lacking any metal coating (e.g. no chrome); the open regions (unshaded) are also transparent, lacking any metal coating; the regions indicated as Mask F are image quality tiles; and regions indicated as Mask A include metal patterns (e.g. chrome). FIG. 12C provides further detail regarding Mask F and Mask A. Generally Mask A and Mask F have a chrome layer (on the inner surface of the upper glass) with optional transparent features as follows. Mask F, which is also referred to as an image quality tile, has a grid of 1.0 $\mu m$ spots spaced 15 $\mu m$ apart in the chrome layer. Mask A includes pattern 1, which includes MTF targets at 5 field points; pattern 2, which is an autofocus tile having a chrome layer with 5 micron holes at 15 micron spacing overlaid with a 500 micron square opening in the center; pattern 3, which is an all chrome layer; pattern 4, which is a chrome layer having a transparent "+" shaped fiducial; and pattern 5, which is a chrome layer having 0.5 micron holes at 15 micron spacing.

Figure 13:
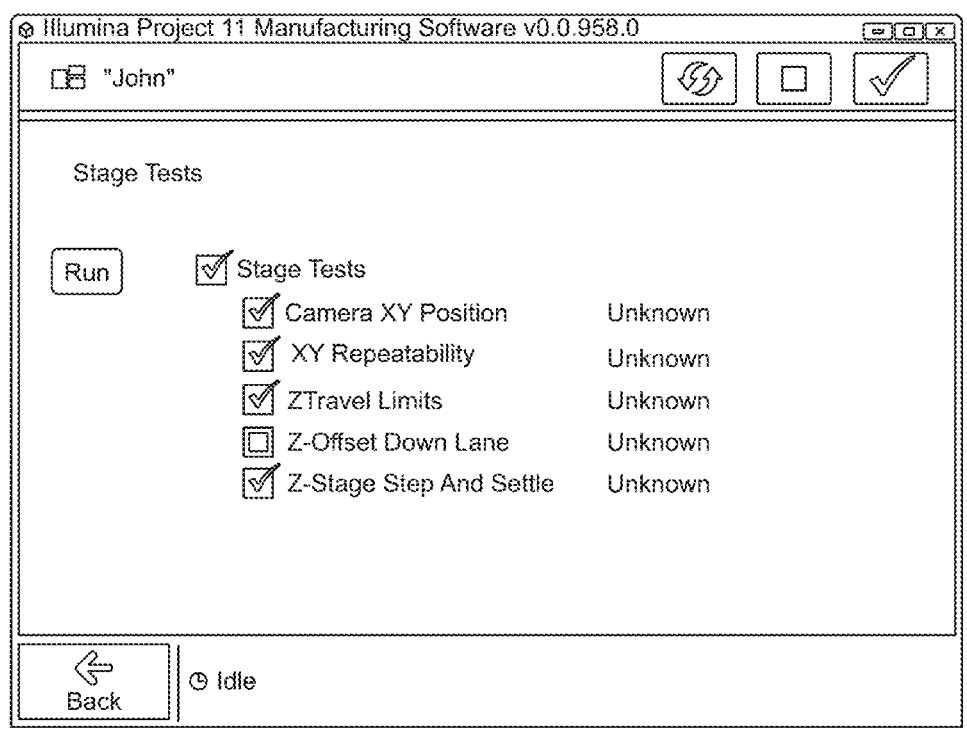
FIG. 13 shows an exemplary graphical user interface for controlling an inspection method on a computer controlled imaging device.

An imaging apparatus can include software for running various inspection methods. The tests can be ordered by an individual via interaction with a graphical user interface (GUI). The GUI can, for example, include a menu of tests from which a user can select some or all tests. An exemplary GUI is shown in FIG. 13. In the GUI a user has clicked on checkbox icons to select four Stage Tests ("Camera XY Position", "XY Repeatability", "Z Travel Limits" and "Z-Stage Step and Settle"). The user has not selected to run the "Z Offset Down Lane" test. By clicking the "Run" button the user can initiate the four tests. The tests can be run by the imaging apparatus and results can be returned to the user, for example, in an XML file format. The results of the test report can be exported to a spreadsheet for further evaluation and analysis.

A system capable of carrying out an inspection method set forth herein, whether integrated with detection capabilities or not, can include a system controller that is capable of executing a set of instructions to perform one or more steps of a method, technique or process set forth herein. For example, the instructions can direct the performance of steps for aligning or validating an optical imaging apparatus. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" can include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming. Software commercially available from Illumina (San Diego), in particular for operating the NextSeq® sequencer is particularly useful.

Figure 14:
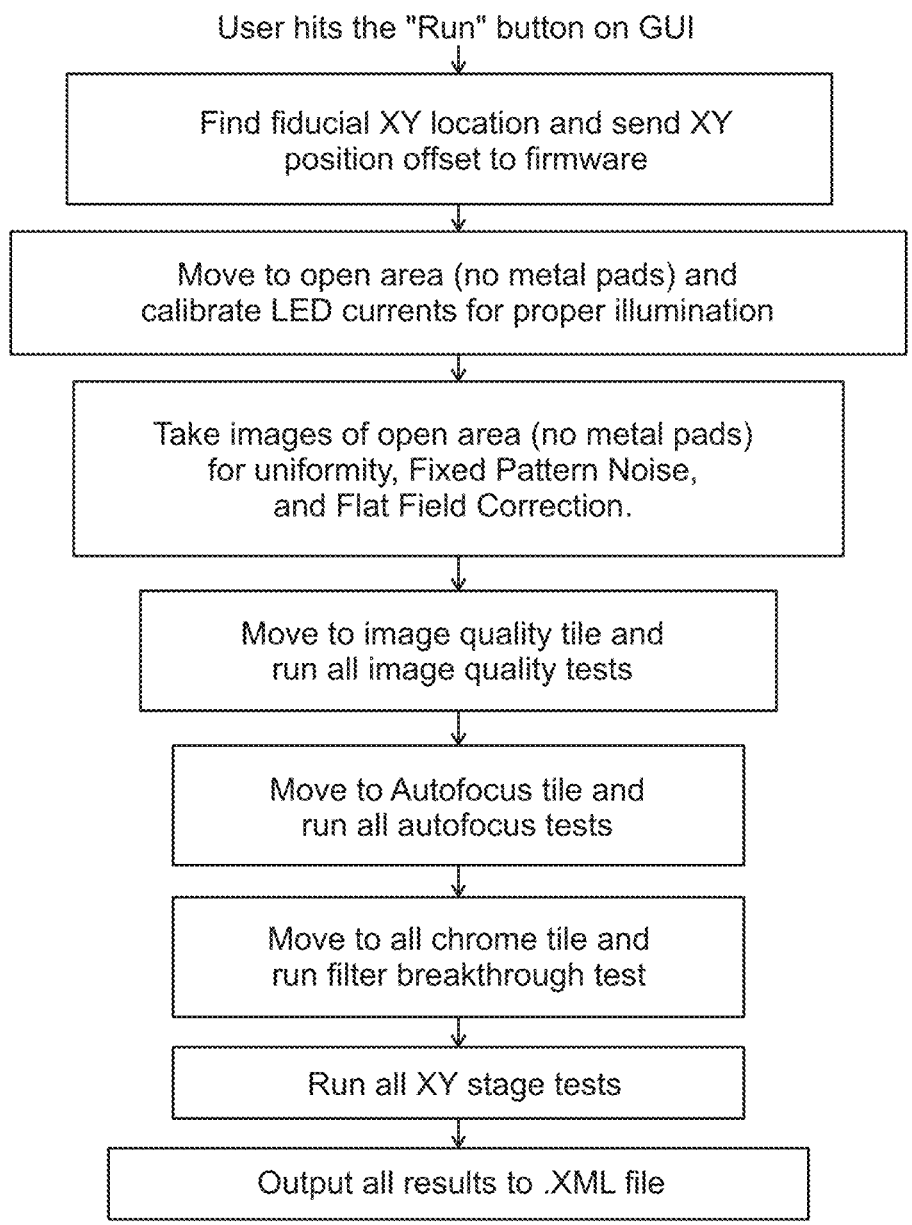
FIG. 14 shows an automated process flow for inspection of a NextSeq® sequencer using an Ubertarget apparatus.

An exemplary automated process flow that can be run on a NextSeq® sequencer and using an Ubertarget apparatus is shown in FIG. 14. The process is initiated in software when the user hits the Run button on the GUI. The imaging module finds the xy position for a fiducial and sends an xy position offset to firmware. This step is not sensitive to image brightness or focus. The xy offset information allows the computer to determine the xy location for all features on the Ubertarget apparatus. The detection area is then moved to an open area of the Ubertarget apparatus (i.e. an area where there are no metal pads) and calibrates the LED currents for the proper illumination. This step is not sensitive to z position. At the next step an image is obtained of the open area to determine image uniformity, fixed pattern noise and flat field correction. These determinations are not sensitive to z position. The process then moves to an image quality tile and image quality tests are run. At this step the best z position is found using a course through-focus stack. Then the imaging window moves to an autofocus tile where autofocus tests are run. After this, images are taken of an area of the Ubertarget apparatus having metal pads and filter breakthrough tests are run. The xy stage tests are then run. After the tests have been run the results are output to an XML file.

Any of a variety of characteristics of an image module can be evaluated using an inspection apparatus of the present disclosure. Several examples are set forth below in the context of testing a NextSeq® sequencer with an Ubertarget apparatus. It will be understood that similar tests can be carried out for other analytical systems using a different inspection apparatus. Furthermore, details of each test need not be necessary n all applications as will be evident to those skilled in the art when applying the principles exemplified below to alternative analytical systems and inspection apparatus.

In some embodiments, optical alignment can be determined. Exemplary aspects of optical alignment that can be evaluated include, image quality as judged by D50/FWHM, usable depth of field, usable field of view, tilt, field curvature, uniformity, chromatism (i.e. axial color), optical distortion, relative camera position, and best focus z position. The D50/FWHM is obtained by imaging features (e.g. the 1.0 micron holes on the image quality tile of an Ubertarget apparatus) and measuring how many pixels occupy the diameter of each feature in the image. For instance, 1 micron holes, when imaged with a relatively high quality camera, will appear to be 1.70 pixels in diameter (FWHM) in the image. If the camera's image quality is poorer, then a larger number of pixels (e.g. 2.00 or more pixels) will appear in the diameter of a 1 micron hole in the image. Another aspect of optical alignment that can be evaluated is encoder error in a moveable stage (e.g. in the Y-stage of the NextSeq® sequencer).

In some embodiments calibration can be evaluated, for example, to determine fixed pattern noise, flat field correction or channel centering. In some embodiments autofocus can be evaluated, for example by determining laser spot z position, autofocus gain, laser spot xy position, laser spot xy separation (when two lasers are used having separated excitation spots), laser spot brightness, laser spot identity and autofocus error. Other verification steps that can be evaluated include, for example, image background, effective field of view, magnification, distortion, z offset down the channel, xy skew, image intensity stability, identification of defective camera pixels, MTF decay time, repeatability of xy movements and accuracy of xy movements.

An inspection method of the present disclosure can include a routine for determining bit error rate. The test sends a known digital pattern through the entire electrical data path of the NextSeq® imaging module from the sensor to the main board RAM and confirms that the pattern read back from RAM is correct.

Fiducial Finding can also be carried out, for example, as follows. A through-focus test is done with 25 micron steps on the xy location where software expects to see the fiducials at lane 1/3, swath 2, tile 1. Course best-focus Z is obtained from the images. Then xy location of the fiducials is determined and used to offset the Ubertarget tile map such that each tile overlays the proper XY coordinate on the Ubertarget being tested.

An inspection method of the present disclosure can include a routine for setting excitation source currents for proper image intensity. The routine can include sequential steps of positioning the Ubertarget apparatus in a NextSeq® imaging module such that an open area of the channel (i.e. with no metal pads) is detected, setting the camera exposure to 1 ms and LED currents to 30%, capturing a dark image with 1 ms exposure and no LEDs on, capturing an image in red and green optical channels with 1 ms exposure, calculating mean intensity of the images, and adjusting LED currents to hit a desired intensity of 2500 counts with 1 ms exposure. LED currents are kept at these values for the remainder of the tests. All subsequent tests can use different exposure times based on the geometry of the metal pad pattern. For example, fiducial tiles and uniformity tiles (lacking metal pads) can be detected with a 1 ms exposure, autofocus tiles can be detected with a 4 ms exposure, image quality tiles can be detected with a 150 ms exposure, and filter breakthrough tiles (fully coated with metal on the interior surface of the upper glass) can be detected with a 500 ms exposure.

An inspection method of the present disclosure can include a routine for excitation source calibration. The routine can be carried out as follows. The xy stage of a NextSeq® sequencer is moved to the autofocus tile at lane 1/3, swath 3, tile 10 of the Ubertarget. A through-focus stack is generated in red and the best-focus Z height is calculated (step size is 6 microns, exposure time is 4 ms and sweep range is 108 micronsO. Then the xy stage is moved to the neighboring tile at lane 1/3, swath 3, tile 9 to collect all laser images. This is done to mitigate the risk of a manufacturing defect in the Ubertarget apparatus where not all the chrome is removed from inside the 500 micron square opening in the autofocus tile. This defect would make the laser spot intensity too bright at the autofocus tile. The process then collects laser through-focus images (using standard settings for focus model generation) and the laser spot intensity is checked. The step size during these measurements is 2 microns with a Z range that is +/−18 microns. Then the laser exposure time is adjusted until the AF spots are 2000+/−200 counts for "brightest spot" (within +/−18 microns of red best focus). If "save calibrations" was selected on the user interface, then the laser exposure time to use for sequencing is stored.

A further routine that can be included in an inspection method is a detector calibration test. The test can be carried out as follows. Images of an Ubertarget apparatus are obtained on a NextSeq® sequencer at 4 different LED intensities: (1) Dark (LEDs off), (2) Middle low intensity, (3) Middle high intensity, and (4) Bright intensity (about 3000 counts). When taking these images the xy stage is moved between each image. All tiles in lane 2/4, all swaths, and tiles 4-11 are used to average out any non-uniform fluorescence (due to debris or fingerprints on top of the Ubertarget). Camera corrections are saved if that was selected in the GUI. Camera corrections need not be applied to any subsequent tests that were selected.

An inspection method of the present disclosure can include a routine for image uniformity correction and flat field correction. Images taken on a NextSeq® sequencer over an Ubertarget tile with no metal pads show relative intensity of the optics across the field of view. For example, fine structure in the illumination for the green LED can be observed as horizontal bands and for the red LED as an outer bright ring. Such images can be used for determining uniformity based on LED positioning, determining fixed pattern noise in the detection device, and determining flat field correction, for example, by calibrating gain and offset of every pixel for each color so that images are equal intensity across the field of view.

Figure 15:
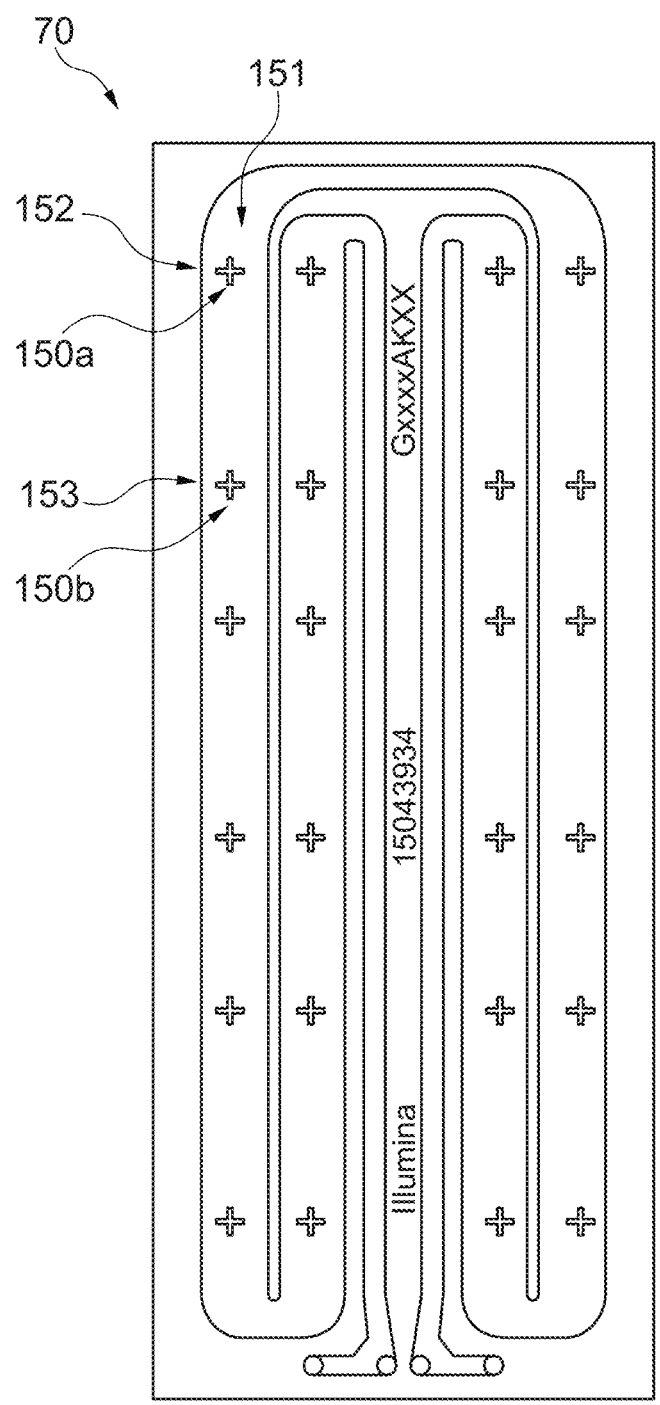
FIG. 15 shows an Ubertarget apparatus having fiducials.

An inspection apparatus can include one or more fiducials in the regions that are to be detected. For example, the Ubertarget apparatus 70 in FIG. 15 has several fiducials that appear as "+" shapes. Fiducial 150a is located at a position that is in the second swath 151 of the first tile 152. Fiducial 150b is also located in the second swath 151 but in the tenth tile 153. The fiducials are arranged with respect to micro fluorometers in a read head of a NextSeq® imaging module such that each camera will observe a fiducial at the second swath of tiles 1 and 10 in each lane of the channel (i.e. where the lanes correspond to the detectable regions of the channels in a NextSeq® flow cell). The fiducial position tolerance is +/−20 μη relative to the reference edges of the Ubertarget apparatus.

A fiducial tile in an inspection apparatus can be used for a variety of evaluations including, for example, determining relative camera position in the x and y dimensions, skew in x and y, and repeatability of repositioning in the positive x direction, negative x direction, positive y direction and negative y direction.

The NextSeq® imaging module shows high accuracy and repeatability for finding fiducials of the Ubertarget apparatus. The fiducials were located 10 times with no change in xy stage motion required. The imaging module produces sharp images with high contrast. The background (i.e. shadow produced by metal regionsO produces an average of 190 counts while the open "+" shaped portion of the fiducial produces 3000 counts.

An inspection method can include an image quality test. The test can be carried out as follows. The stage of a NextSeq® sequencer is moved to the image quality tile (lane 1/3, swath 2, tile 4) of the Ubertarget apparatus. A course-focus is performed using red excitation to find best focus to within a few microns (step size is set to 6 microns, exposure time is set to 150 ms and LED currents are set to the values calculated during LED calibration). A fine through-focus stack is collected in red and green (step size is set to 1 micron, exposure time is set to 150 ms and LED currents are set to the values calculated during LED calibration). Image processing is performed on the fine though-focus images to determine FWHM best focus average in the red channel, FWHM best focus average in the green channel, chromatism, and best focus z top in the green channel.

A laser z bias test can also be performed, for example, as follows. The xy stage of a NextSeq® sequencer is moved to the autofocus tile at lane 1/3, swath 3, tile 10 of the Ubertarget apparatus. Course through-focus is done in the red channel to determine the approximate best-focus point for red. Fine through-focus is done in red to determine the best-focus Z height for red (step size is 2 microns, exposure time is 4 ms, LED current is set to the value determined during LED calibration). Laser through focus is performed as a step size of 5 microns with exposure time set to the value determined during laser calibration. Laser images are analyzed to determine the z coordinate where the laser spot from top surface is at best-focus. If undesirable results are obtained, then the laser through-focus stack is repeated at the neighboring tile at lane 1/3, swath 3, tile 9 of the Ubertarget.

An inspection method of the present disclosure can include a routine for testing the camera-to-camera XY offset. The NextSeq® imaging module contains 6 microfluorometers in a monolithic read head, each microfluorometer having a dedicated camera. The results of this routine will indicate the relative xy position of the camera detection zones at the sample stage. The routine can be carried out as follows. The xy stage is positioned so all cameras are looking at their first lane, first tile fiducials in the Ubertarget apparatus. Fiducial images are captured for all cameras. Fiducial xy locations are calculated for each camera. Camera 2 is used as a reference and all other cameras' xy offsets are calculated relative to camera 2. Repeatability of this routine was found to result in a variance of less than 1 μη in the x and y dimensions.

Figure 16A:
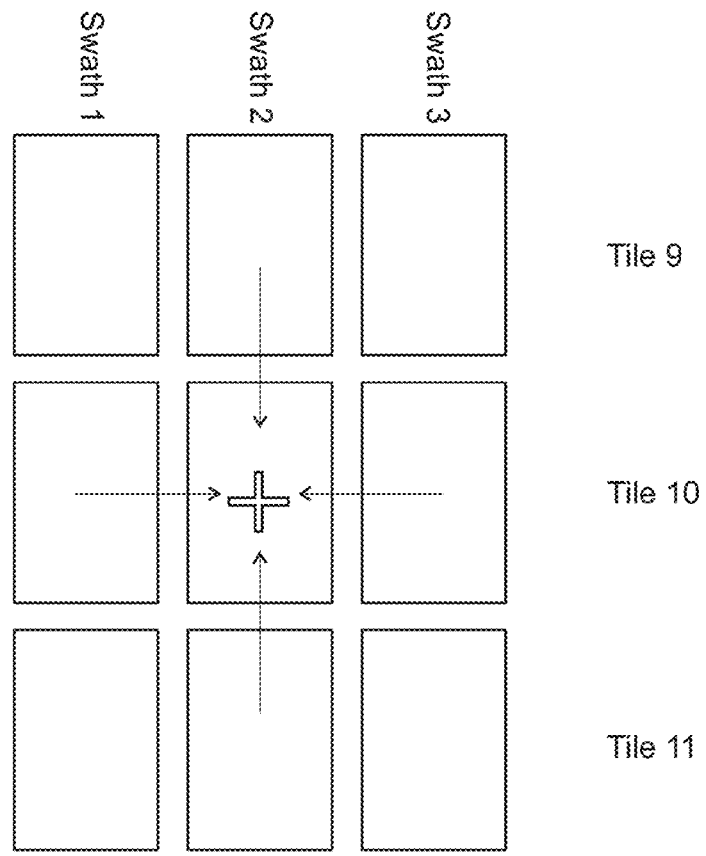
FIG. 16A shows directions of movement for determining hysteresis in locating a fiducial.
Figure 16B:
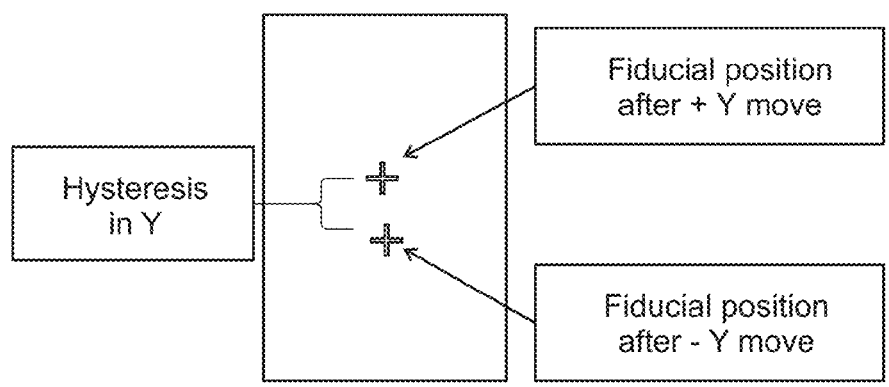
FIG. 16B shows hysteresis in images obtained when locating a fiducial.

A further routine that can be included in an inspection method is determination of xy stage position repeatability and hysteresis. The results of the test will indicate how repeatably the xy stage can be correctly positioned when approaching a location from different directions. This will indicate how much hysteresis (slop) is in the stage's movement. The routine can be carried out as follows in reference to FIG. 16A. The test is conducted using camera 2, lane 1, starting at swath 2, tile 10, which has a fiducial as indicated by the "+"symbol in FIG. 16A. The xy stage is moved one tile over from target tile 10, then moved back to the target tile and the xy position of the fiducial is recorded. This test is repeated 30 times, approaching the target tile from all 4 directions as indicated by the arrows in FIG. 16A. The xy position repeatability for each stage position is the standard deviation of the fiducial position after the move. Hysteresis is the difference between fiducial average positions when approaching from the positive and negative directions. FIG. 16B shows hysteresis in the y dimension that is identified from fiducial position changes in images due to movement in the positive and negative directions of the xy stage along they dimension. Repeatability of this routine was found to result in a variance of less than 1 μη in the x and y dimensions.

An xy stage test for z wedge down the lane and between lanes can also be performed. The results of the test indicate the change in best-focus z position going down the length of the lanes and going from lane 1 to lane 2 (i.e. from the region of the Ubertarget apparatus corresponding to the first channel of a flow cell to the region corresponding to the second channel of the flow cell). The test procedure uses camera 2. Through-focus is done on the fiducial and best-focus z is calculated at the following tiles: lane 1, swath 2, tiles 1 and 10 and lane 2, swath 2, tile 1. The z wedge down the lane is the change in best-focus z between tile 1 and tile 10. The z wedge from lane to lane is the change in best-focus z between lane 1 and lane 2. The measurement repeatability using the Ubertarget apparatus on the NextSeq® imaging module was found to be 16 nm (1 σ) for best-focus z position at each location.

A test for autofocus error can be performed. For example, the test can be done by moving the xy stage of a NextSeq® sequencer to the autofocus tile at lane 1/3, swath 3, tile 1 of the Ubertarget apparatus. A course through-focus is done in the red channel to determine approximate best z. A focus model is generated using default settings (step size is 2 microns and z range is +/−18 microns). Two hundred random moves in the z dimension are performed in the range of +/−20 microns from best-focus. After each move, a laser image is captured and the distance from best-focus is calculated using the focus model. The calculated distance to move is compared to the known random move that was performed. The z stage is moved by the calculated distance from best focus. Another laser image is obtained and the distance from best-focus is calculated using the focus model. The calculated distance from best focus is compared to the actual best-focus position.

Focus model repeatability can be tested in a routine, for example, as follows. The xy stage of a NextSeq® sequencer is moved to the autofocus tile at lane 1/3, swath 3, tile 1 of the Ubertarget apparatus. A course through-focus is done in the red channel to determine approximate best z. A focus model is generated using default settings (step size is 2 microns and z range is +/−18 microns). The xy stage is moved to the extremes of travel in both dimensions and then back to the autofocus tile at lane 1/3, swath 3, tile 1. This is intended to simulate vibration in the optics in the same manor that may occur during an analytical procedure (e.g. nucleic acid sequencing). The steps of generating the focus model and moving the xy stage to extremes of travel are repeated 20 times. The y spot position at best focus and the focus model gain are compared from each of the focus models that were generated.

Figure 17:
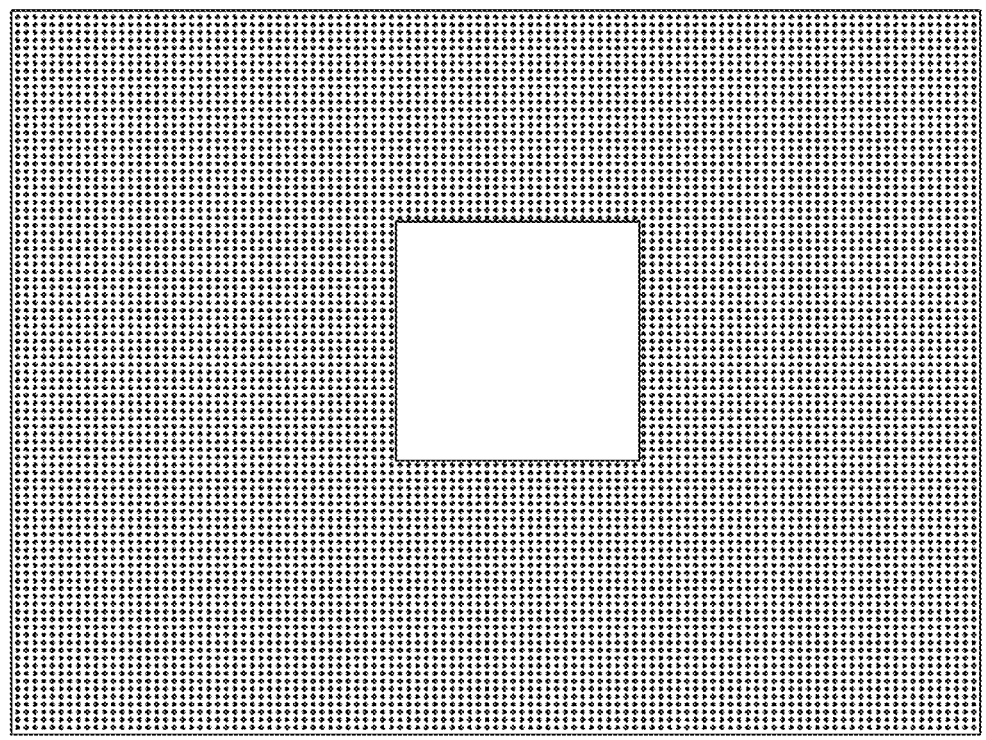
FIG. 17 shows an image of an autofocus tile of an Ubertarget apparatus.

FIG. 17 shows an image of an autofocus tile of the Ubertarget apparatus. The tile includes a chrome covered area with 5 micron holes at 15 micron spacing. The resulting pattern can be used to determine best focus. The middle of the image shows a relatively large opening in the chrome pattern. The opening allows the autofocus laser of each microfluorometer in the NextSeq® imaging module to pass through and generate lane top and lane bottom reflections. The shape and sharpness of the resulting images are used to determine focus.

Figure 18:
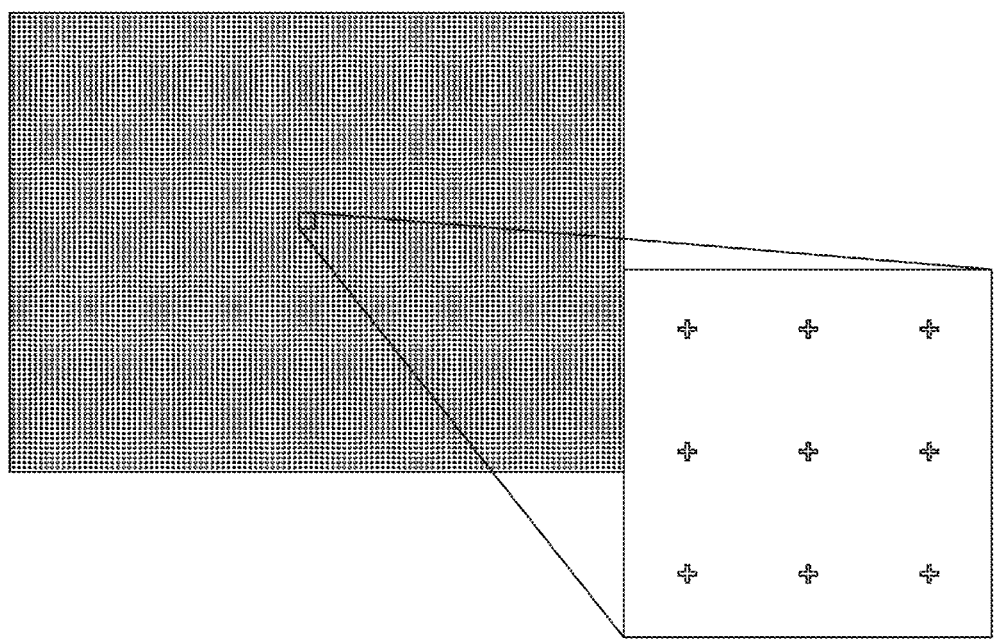
FIG. 18 shows an image of an image quality tile of an Ubertarget apparatus.

A photograph of an image quality tile is shown in FIG. 18. A relatively large field of view is shown in the left image along with a higher magnification image at the right. The image is produced from a tile having a chrome coating with 1 micron holes spaced 15 microns apart. In particular embodiments the tolerance in hole size variation is +/−50 nm, which allows for a desired level of accuracy in calibration measurements. The resulting square grid of objects is useful for revealing barrel distortion in an imaging system. The holes produce spots in the image that produce about 3300 counts on the imaging system whereas the background (interstitial) areas produce 400 counts.

Simple object detection and analysis was successful using the Ubertarget image quality through-focus test. The consistency of object spacing and object sizes in the Ubertarget image quality tile enabled analyzing the images at finer detail. Images were analyzed on a 18×24 grid. This results in detection of about 30 objects per subtile.

The optical density of the chrome layer on the Ubertarget apparatus was measured using a green laser of the NextSeq® imaging module focused onto the filter breakthrough tile. The power measured through a tile with no chrome was 4.10 mW. The power measured through the filter breakthrough tile (all chrome) was far lower at 0.020 mW. From this test it was determined that radiation density of 1 part in 500 makes it through the chrome (i.e. an optical density of 2.3).

An inspection method of the present disclosure can include a routine for determining autofluorescence and filter breakthrough. The test can be used to determine how much excitation light (e.g. from an LED of a NextSeq® imaging module) makes it to a detector (e.g. a camera of a NextSeq® imaging module). The test can also indicate how much the Ubertarget apparatus glass autofluoresces. The test can be carried out on a NextSeq® imaging module as follows. Measurements are taken with LEDs at 50% current and exposure time of 999 ms. An image is obtained with the LEDs off to provide a dark read. Then an image is obtained over the mirrored surface provided at the filter breakthrough tile (solid chrome layer). This measurement indicates how much LED light gets to the sensor. Then an image is obtained over the open area of the lane with no chrome (uniformity tile). This measurement indicates how much the Ubertarget apparatus glass autofluoresces. Then an image can be obtained with the Ubertarget apparatus removed. This measurement indicates how much of the detected signal is due to the fixturing of the image module. The resulting measurements are shown in Table I.

TABLE I

Autofluorescence and filter breakthrough experiment results

| Measurement condition | Green Intensity (counts) | Red Intensity (counts) |
|---|---|---|
| LEDs off | 170 | 170 |
| Solid chrome (filter breakthrough) tile with no dye solution in lane | 1300 | 1100 |
| Chrome-free (uniformity) tile with no dye solution in lane | 1050 | 800 |
| With Ubertarget apparatus removed | 650 | 600 |

The results of Table I indicate that the autofluorescence of the Ubertarget apparatus glass is 400 counts (green channel) and 200 counts (red channel). The amount of LED light that reflects off the chrome and hits the sensor is 700 counts (green channel) and 700 counts (red channel).

Nearly all measurements taken on the NextSeq imaging module using the Ubertarget apparatus were highly repeatable, indicating a robust tool for investigating image system performance.

Throughout this application various publications, patents and patent applications have been referenced. Their disclosures are hereby incorporated by reference in this application, in their entireties, in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:
1. An inspection apparatus comprising:
a translucent or transparent plate having a bottom surface, at least a portion of the bottom surface having an opaque material printed thereon in a pattern having at least one transparent or translucent portion;
a channel disposed below the bottom surface, wherein the channel comprises one or more lanes, whereby light emitted from the channel or through the channel can pass through the at least one transparent or translucent portion of the pattern;

a fluid filling at least a portion of the channel, the fluid comprising at least one light emitting material, the fluid to emit fluorescence in response to excitation light, the channel having fluid entry and exit ports that are closed.

2. The apparatus of claim 1, wherein the fluid entry and exit ports that are closed with a sealant.

3. The apparatus of claim 1, wherein the fluid comprises first and second fluorescent dyes to emit first and second emissions in response to first and second excitation light sources, respectively.

4. The apparatus of claim 1, wherein the light emitting material comprises one or more fluorescent or luminescent molecules.

5. The apparatus of claim 4, wherein the fluorescent molecules are selected from the group consisting of a Rhodamine dye and an Oxazine dye.

6. The apparatus of claim 1, wherein the pattern comprises a plurality of translucent or transparent holes in an ordered array.

7. The apparatus of claim 1, wherein the channel comprises a plurality of parallel lanes that are connected to form a single chamber.

8. The apparatus of claim 1, wherein the channel includes a detection lane positioned between an ingress lane and an egress lane, the ingress and egress lanes having a length to prevent bubbles from encroaching into the detection lane.

9. The apparatus of claim 8, wherein the detection lane that is relatively wide compared to the ingress lane and the egress lane that are relatively narrow.

10. The apparatus of claim 8, wherein the ingress and egress lanes connect the detection lanes to ingress and egress ports respectively.

11. A method of evaluating an imaging module comprising:

positioning an imaging module in optical alignment with an inspection apparatus that comprises: (a) a translucent or transparent plate having a bottom surface, at least a portion of the bottom surface having an opaque material printed thereon in a pattern having at least one transparent or translucent portion; (b) a channel disposed below the bottom surface, wherein the channel comprises one or more lanes, whereby light emitted from the channel or through the channel can pass through the at least one transparent or translucent portion of the pattern; and (c) a fluid filling at least a portion of the channel, the fluid comprising at least one light emitting material, the fluid to emit fluorescence in response to excitation light, the channel having fluid entry and exit ports;

detecting light transmitted through one or more of the transparent or translucent portions; and based on the light that is detected, performing at least one of: i) determining an accuracy of the optical alignment based on the light that is detected, ii) determining an autofocus accuracy of a detector that detects the light that is detected, or iii) finding a fiducial on the inspection apparatus based on the light that is detected.

12. The method of claim 11, further comprising setting excitation source currents based on the light that is detected when using the excitation source to irradiate the inspection apparatus.

13. The method of claim 11, further comprising calibrating an excitation source based on the light that is detected when using the excitation source to irradiate the inspection apparatus.

14. The method claim 11, further comprising calibrating a detector that detects the light that is detected.

15. The method of claim 11, further comprising determining at least one of:
  i) an image uniformity correction or flat field correction based on the light that is detected;
  ii) z bias in an excitation source based on the light that is detected when using the excitation source to irradiate the inspection apparatus;
  iii) camera-to-camera xy offset based on the light that is detected;
  iv) repeatability of xy stage positioning or hysteresis in xy stage positioning based on the light that is detected; or
  v) focus repeatability based on the light that is detected.

16. The method of claim 11, wherein the fluid entry and exit ports that are closed with a sealant.

17. The method of claim 11, wherein the light emitting material comprises one or more fluorescent or luminescent molecules.

18. The method of claim 11, wherein the pattern comprises a plurality of translucent or transparent holes in an ordered array.

19. The method of claim 11, wherein the channel comprises a plurality of parallel lanes that are connected to form a single chamber.

20. The method of claim 11, wherein the channel includes a detection lane positioned between an ingress lane and an egress lane, the ingress and egress lanes having a length to prevent bubbles from encroaching into the detection lane.

* * * * *

UNITED STATES PATENT AND TRADEMARK OFFICE
CERTIFICATE OF CORRECTION

PATENT NO. : 10,005,083 B2
APPLICATION NO. : 15/382684
DATED : June 26, 2018
INVENTOR(S) : John Earney et al.

Page 1 of 1

It is certified that error appears in the above-identified patent and that said Letters Patent is hereby corrected as shown below:

In the Specification

In Column 1, Lines 3-6, delete "This application is based on, and claims the benefit of, U.S. Provisional Application No. 61/871,181, filed Aug. 28, 2013, which is incorporated herein by reference in its entirety." and insert -- CROSS-REFERENCE TO RELATED APPLICATIONS This application is a continuation application of, and claims benefit to the filing date of, U.S. Patent Application Serial No. 14/906,536, filed January 20, 2016, entitled "OPTICAL ALIGNMENT TOOL", which is a national stage filing under 35 U.S.C. § 371 of International Patent Application No. PCT/US2014/053124, filed August 28, 2014, which is based on, and claims the benefit of, U.S. Provisional Application No. 61/871,181, filed August 28, 2013, the entire disclosures of which are incorporated by reference herein. --, therefor.

In the Claims

In Column 28, Line 20, in Claim 14, after "method" insert -- of --.

Signed and Sealed this
Thirteenth Day of November, 2018

Andrei Iancu
*Director of the United States Patent and Trademark Office*